(12) United States Patent
Bigio et al.

(10) Patent No.: US 9,072,428 B2
(45) Date of Patent: Jul. 7, 2015

(54) CLASSIFICATION TECHNIQUES FOR MEDICAL DIAGNOSTICS USING OPTICAL SPECTROSCOPY

(75) Inventors: Irving Bigio, Chestnut Hill, MA (US); Eladio Rodriguez-Diaz, Brookline, MA (US); David Castanon, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 698 days.

(21) Appl. No.: 13/259,094

(22) PCT Filed: Mar. 25, 2010

(86) PCT No.: PCT/US2010/028741
§ 371 (c)(1),
(2), (4) Date: Apr. 12, 2012

(87) PCT Pub. No.: WO2010/111545
PCT Pub. Date: Sep. 30, 2010

(65) Prior Publication Data
US 2012/0191635 A1     Jul. 26, 2012

Related U.S. Application Data

(60) Provisional application No. 61/163,423, filed on Mar. 25, 2009.

(51) Int. Cl.
A61B 5/00 (2006.01)
G06N 99/00 (2010.01)
G06K 9/00 (2006.01)
G06K 9/62 (2006.01)

(52) U.S. Cl.
CPC .............. *A61B 5/0059* (2013.01); *G06N 99/00* (2013.01); *A61B 5/415* (2013.01); *A61B 5/418* (2013.01); *A61B 5/7267* (2013.01); *G06K 9/00147* (2013.01); *G06K 9/6256* (2013.01); *G06K 9/6269* (2013.01)

(58) Field of Classification Search
CPC ....................................................... G06F 15/18
See application file for complete search history.

(56) References Cited

U.S. PATENT DOCUMENTS 7,282,723 B2    10/2007  Schomacker et al.
2004/0010375 A1*  1/2004  Schomacker et al. .......... 702/19
2008/0194969 A1*  8/2008  Werahera et al. ............. 600/476

OTHER PUBLICATIONS

Cortes, C. et al. "Support-vector networks." Machine learning vol. 20 No. 3 pp. 273-297, 1995.*
Grandvalet, Y. et al. Support Vector Machines with a Reject Option. In NIPS (pp. 537-544), 2008.*
Grandvalet, Y., et al. "Support vector machines with a reject option." Advances in neural information processing systems. 2009.*

(Continued)

*Primary Examiner* — Kakali Chaki
*Assistant Examiner* — Eric Nilsson
(74) *Attorney, Agent, or Firm* — Nixon Peabody LLP; Ronald I. Eisenstein; Leena H. Karttunen Contarino

(57) ABSTRACT

Mathematical/statistical pattern-recognition systems and methods to distinguish between different pathologies and benign conditions (e.g., normal or cancerous tissue) given spectra measured using optical spectroscopy such as elastic-scattering spectroscopy (EES).

20 Claims, 17 Drawing Sheets

(56) References Cited

OTHER PUBLICATIONS

Silla, C., et al. "Automatic music genre classification using ensemble of classifiers." Systems, Man and Cybernetics, 2007. ISIC. IEEE International Conference on. IEEE, 2007.*

Dietterich, T, et al. "Ensemble methods in machine learning." Multiple classifier systems. Springer Berlin Heidelberg, 2000. pp. 1-15.*

Teh, S. et al. "Spectroscopic diagnosis of laryngeal carcinoma using near-infrared Raman spectroscopy and random recursive partitioning ensemble techniques." Analyst 134.6 (2009): 1232-1239.*

Tumer, K., et al. "Ensembles of radial basis function networks for spectroscopic detection of cervical precancer." Biomedical Engineering, IEEE Transactions on 45.8 (1998): 953-961.*

Yves Grandvalet, et al, "Support Vector Machines with a reject option", Advances in neural information processing systems 21, pp. 537-544, 2009.

* cited by examiner

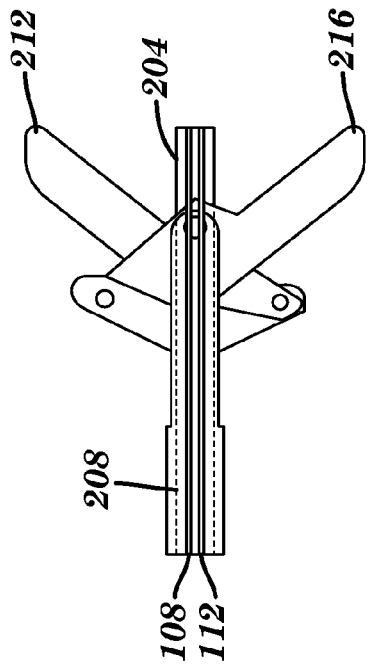
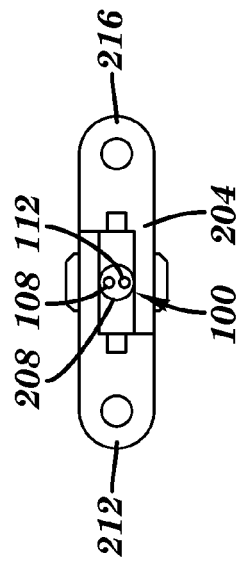
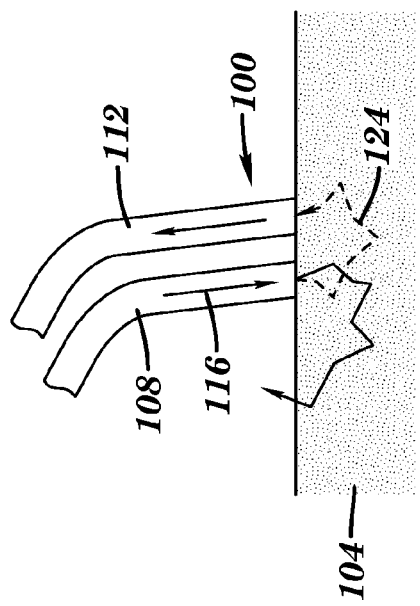
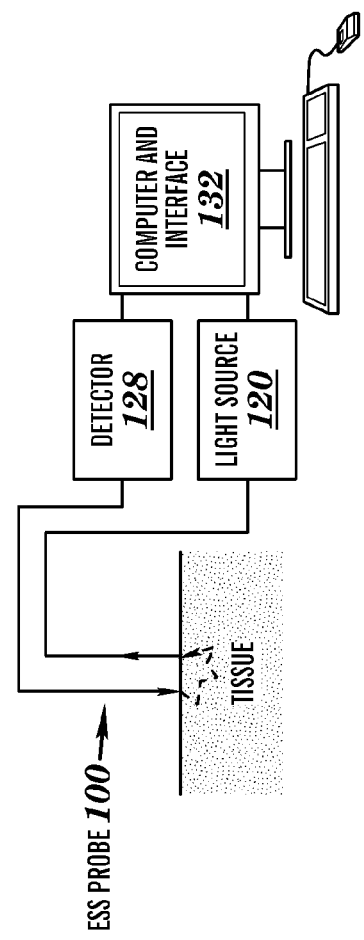

SFFS ALGORITHM

INPUT:
$$Y = \{y_j \mid j = 1,...,D\}$$

OUTPUT:
$$X_k = \{x_j \mid j = 1,...,k, x_j \in Y\}, k = 0,1,...,D$$

INITIALIZATION:
$$X_0 = \emptyset; k = 0$$

TERMINATION:
STOP WHEN k EQUALS THE NUMBER OF DESIRED FEATURES.

STEP 1: INCLUSION $$x^+ = \operatorname*{argmax}_{x \in Y-X_k} J(X_k + x)$$ } THE MOST SIGNIFICANT FEATURES WITH RESPECT TO $X_K$ $$X_{k+1} = X_k + x^+; \quad k = k+1$$

STEP 2: CONDITIONAL EXCLUSION $$x^- = \operatorname*{argmax}_{x \in X_k} J(X_k - x)$$ } THE LEAST SIGNIFICANT FEATURES IN $X_K$ $$\text{if } J\left(X_k - \{x^-\}\right) > J(X_{k-1}) \text{ then}$$

$$X_{k-1} = X_k - x^-; \quad k = k-1$$

GO TO STEP 2

*else*

GO TO STEP 1

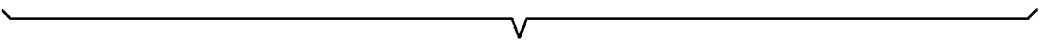

*FIG. 4*

SVDSS ALGORITHM:

INPUTS:

$X = [x_1, x_2, L, x_N]$, WHERE $x_n$ IS A FEATURE VECTOR OF d DIMENSIONS.

p, DESIRED NUMBER OF FEATURES, p = d.

1. PERFORM STANDARD NORMAL NORMALIZATION ON THE COLUMNS OF X.

2. COMPUTE THE SVD OF $X = U\Sigma V^T$.

3. COMPUTE THE QR FACTORIZATION WITH PIVOTING OF $V_p$, WHERE $V_p$ IS FORMED BY THE FIRST p COLUMNS OF V.

4. COMPUTE $\bar{X} = P^T X$ WHERE P IS THE PIVOTING MATRIX OBTAINED IN THE PREVIOUS STEP.

5. SELECT THE FIRST p COLUMNS OF $\bar{X}$ AS THE NEW FEATURES.

*FIG. 5*

Procedure to Analytically Optimize Two Lagrange Multipliers:

Step 1: Determine the initial value of $\frac{\partial}{\partial \alpha_2} g(\alpha_2, \varepsilon)$ and $\frac{\partial}{\partial \alpha_1} g(\alpha_1, \varepsilon)$ based on the interval where $\alpha_2$ and $\alpha_1$ lies.

Step 2: Compute $\alpha_2^{new} = \alpha_2 - \frac{1}{\eta}\left(y_2(E_1 - E_2) + \frac{\partial}{\partial \alpha_2} g(\alpha_2, \varepsilon_2) - s\frac{\partial}{\partial \alpha_1} g(\alpha_1, \varepsilon_1)\right)$ with the values of $\frac{\partial}{\partial \alpha_2} g(\alpha_2, \varepsilon)$ and $\frac{\partial}{\partial \alpha_1} g(\alpha_1, \varepsilon)$ as determined in Step 1.

Step 3: Clip $\alpha_2^{new}$ as to $L \leq \alpha_2^{new} \leq H$.

Step 4: Compute $\alpha_1^{new} = \alpha_1 + s(\alpha_2 - \alpha_2^{new})$.

Step 5: Determine initial ascent direction as $\text{sgn}(\alpha_2^{new} - \alpha_2)$.

Step 6: Check that $\alpha_2^{new}$ and $\alpha_1^{new}$ lies within the current interval:

1. If $\alpha_2^{new}$ and $\alpha_1^{new}$ lie within the current interval;
   Then Stop, maximum has been found.

2. If $\alpha_2^{new}$ is greater than the upper bound;
   Then $\alpha_2^{new}$ = upper bound and recompute $\alpha_1^{new} = \alpha_1 + s(\alpha_2 - \alpha_2^{new})$.

3. If $\alpha_1^{new}$ is greater than the upper bound;
   Then $\alpha_1^{new}$ = upper bound and recompute $\alpha_2^{new} = \alpha_2 + s(\alpha_1 - \alpha_1^{new})$.

*FIG. 9*

Step 7: Compute $\alpha_2^{next} = \alpha_2 - \dfrac{1}{\eta}\left(y_2(E_1 - E_2) + \dfrac{\partial}{\partial \alpha_2}g(\alpha_2^{next},\varepsilon_2) - s\dfrac{\partial}{\partial \alpha_1}g(\alpha_2^{next},\varepsilon_1)\right)$ with the values of $\dfrac{\partial}{\partial \alpha_2}g(\alpha_2^{next},\varepsilon)$ and $\dfrac{\partial}{\partial \alpha_1}g(\alpha_1^{next},\varepsilon)$ determined by the subsequent intervals based on the ascent direction.

1. Clip $\alpha_2^{next}$ as to $L \le \alpha_2^{next} \le H$.

2. Determine the ascent direction $\operatorname{sgn}(\alpha_2^{next} - \alpha_2^{new})$ If the ascent direction changes;
    Then Stop, maximum has been found;
    Else    set $\alpha_2^{new} = \alpha_2^{next}$, compute $\alpha_1^{new} = \alpha_1 + s(\alpha_2 - \alpha_2^{new})$,
          Go to Step 6.

*FIG. 9 (cont.)*

KKT Violations:

Let $R_i = y_i(\mathbf{w}^t \mathbf{x}_i - b) - 1$, i. If $\alpha_i > 0$ and $R_i > 0$
ii. If $\alpha_i < Cw_c$ and $R_i < 0$
iii. If $Cw_c < \alpha_i < Cw_r$ and $R_i \neq -(1-\varepsilon)$
iv. If $Cw_r < \alpha_i < Cw_e$ and $R_i \neq -(1+\varepsilon)$
v. If $\alpha_i = Cw_c$ and $R_i \geq 0$ or $R_i \leq -(1-\varepsilon)$
vi. If $\alpha_i = Cw_r$ and $R_i \geq -(1-\varepsilon)$ or $R_i \leq -(1+\varepsilon)$
vii. If $\alpha_i = Cw_e$ and $R_i \geq -(1+\varepsilon)$

*FIG. 10*

AdaBoost Training Algorithm

Input: Training samples $(\mathbf{x}_i, y_i)$ for $i = 1, \cdots, l$

Initialize: $w_1(\mathbf{x}_i) = 1/l$ for $i = 1, \cdots, l$

Do for $t = 1, \cdots, T$

1. Train base learner with respect to weighted sample set $\{\mathbf{x}_i, y_i, \mathbf{w}_t\}$ and obtain hypothesis $g_t : \mathbf{x} \mapsto \{\pm 1\}$ 2. Calculate the training error $e_t$ of $g_t$:

$$e_t = \sum_{i=1}^{l} w_t(\mathbf{x}_i) I(g_t(\mathbf{x}_i) \neq y_i),$$

abort if $e_t = 0$ or $e_t \geq 1/2 - \Delta$, where $\Delta$ is a small constant.

3. Set $$b_t = \log \frac{(1 - e_t)}{e_t}$$

4. Update weights $\mathbf{w}_t$:

$$w_{t+1}(\mathbf{x}_i) = w_t(\mathbf{x}_i) \exp\{-b_t I(g_t(\mathbf{x}_i) = y_i)\}/Z_t$$

where $Z_t$ is a normalization constant, such that $\sum_{i=1}^{T} w_{t+1}(\mathbf{x}_i) = 1$.

Output: Final hypothesis $$f(\mathbf{x}) = \sum_{t=1}^{T} c_t g_t(\mathbf{x}), \qquad \text{where} \qquad c_t = \frac{b_t}{\sum_{t=1}^{T} |b_t|}$$

*FIG. 14*

CLASSIFICATION TECHNIQUES FOR MEDICAL DIAGNOSTICS USING OPTICAL SPECTROSCOPY

PRIORITY

This application is a National Phase of International Application No. PCT/US2010/028741, which was filed on Mar. 25, 2010, and claims the benefit of U.S. Provisional Application No. 61/163,423, filed Mar. 25, 2009, entitled "Pattern Recognition Algorithms for Spectral Classification with Applications to Detections/Screening of Cancer and Other Pathologies Using Optical Spectroscopy," and the disclosures of which are hereby incorporated herein by reference in their entireties.

GOVERNMENT SUPPORT

This invention was made with Government Support under Contract No. CA104677 awarded by the National Institutes of Health. The Government has certain rights in the invention.

BACKGROUND

1. Field

The subject invention relates to systems and methods for classifying optical spectroscopy image data of biological tissues such as cancer and other pathologies for medical diagnostics.

2. Related Art

Current screening for early detection of breast cancer, for example, is based on either abnormalities visible in a mammography or lumps detected by the patients or doctors using palpation. Before any treatment is initiated, the diagnosis must be confirmed. This is usually accomplished by performing a biopsy, which is an invasive procedure, and then determining the histology of the tumor. A less invasive alternative is the use of fine-needle aspiration cytology (FNA). FNA is infrequently used, however, due to a significant false-negatives rate. Approximately 50,000 diagnostic lumpectomies are performed annually in the U.S. Of those, only about 12,000 turn out to be malignant when histology is performed by a pathologist. If it had been known in advance that the remaining 38,000 lesions were benign, the potentially disfiguring surgery could have been avoided, as many benign lesions resolve spontaneously in time, without intervention.

Cervical cancer is the third most common cancer in women worldwide and is the leading cause of cancer mortality for women in developing countries. When precancerous lesions are detected early they are easily treatable by ablation or excision. At more advanced stages, cervical cancer often requires hysterectomy, chemotherapy, radiation therapy, or combined chemo-radiation therapy. Current screening for this type of cancer is accomplished first by a Papanicolaou (Pap) smear, with sensitivities and specificity values ranging from 11% to 99% and 14% to 97% respectively, and results usually available in two weeks. The second stage of the screening process, after an abnormal Pap smear, is a colposcopy. This test has an excellent sensitivity (>90%) but poor specificity (<50%), even in the hands of an experienced practitioner. Because of the poor specificity, a biopsy is required to confirm the diagnosis. Currently, women often wait up to eight weeks to be treated as part of the standard care in the diagnosis and treatment of cervical cancer after an abnormal Pap smear.

Barrett's Esophagus is a pre-cancerous condition that is an important risk factor in developing esophageal adenocarcinoma, the most common form of esophageal cancer. It is associated with chronic gastrointestinal reflux disease and is increasing in incidence in western countries. The development of malignancy is thought to be a progression from nondysplaic Barrett's mucosa, through low-grade dysplasia (LGD) to high-grade dysplasia (HGD), to carcinoma. Consequently, it is critical to identify patients with Barrett's esophagus that are most at risk of developing cancer. Patches of dysplasia within a section of Barrett's mucosa cannot be detected visually using conventional white light endoscopy. Diagnosis requires multiple random biopsies and subsequent histological examination. As many as 20-30 "random" biopsies may be taken in one session. This is a time consuming (and expensive) procedure, which entails some degree of risk for the patient. For each conventional biopsy, the biopsy tool must be withdrawn from the endoscope and the specimen removed before the tool can be reinserted for the next biopsy. Because biopsies are taken at random from within a section of Barrett's esophagus, detection of pre-cancerous changes is relatively poor.

In recent years, several spectroscopy techniques have been proposed as potential methods for distinguishing between different tissue pathologies. The motivation of these techniques is to reduce, or eliminate, the need for surgical removal of biopsy tissue samples. Instead, some form of spectral analysis of the tissue is applied to measurements obtained with an optical probe placed on or near the surface of the tissue in question. A diagnosis of the tissue is then attempted based on these measurements, in situ, noninvasively and in real time. Additionally, there is the potential for reduced health care cost and patient distress as a consequence of the reduced need for histology and the need for the surgical environment required to take the biopsy samples. Some of these proposed spectroscopic techniques include Raman spectroscopy, autofluorescence spectroscopy, fluorescence spectroscopy, reflectance spectroscopy, and elastic-scattering spectroscopy.

Screening and/or detection of cancer at an early stage is of significant importance as many incidences of the disease can be treated successfully at early stages. In recent years, these optical spectroscopy methods have received increased attention for this purpose, due to the fact that they possess some desirable properties—they are noninvasive, in situ, and results can be obtained almost in real time. These methods provide data sensitive to changes of the underlying tissue (e.g. structural, biochemical), which can be exploited for the development of diagnostic algorithms. Various statistical pattern recognition and machine learning methods have been used to develop these diagnostic algorithms.

For example, A MAP (Maximum A-Posteriori) classifier was used to distinguish between squamous intraepithelial lesions (SILs) and normal squamous epithelia, and to distinguish between high-grade squamous intraepithelial lesions (HGSILs) and low-grade squamous intraepithelial lesions (LGSILs) using fluorescence spectroscopy applied to cervical tissue. Posterior probabilities were computed after fitting the training data to a gamma function. A sensitivity and specificity of 82% and 68%, respectively, for the first case and of 79% and 78% for the second case were reported.

Linear discriminant analysis has also been used. A classification accuracy of 72% was reported for distinguishing malignant melanoma from benign nevi in the skin using reflectance spectra. Elastic-scattering spectroscopy was used to detect dysplasia in the esophagus. Sensitivity of 77% and specificity of 77% were obtained in detecting "high risk" biopsies. The same spectroscopy technique has been employed to detect cancer in the sentinel lymph node for breast cancer, with a resulting sensitivity of 75% and specificity of 89%.

Fisher's linear discriminant has also been used. This method obtains the linear function yielding the maximum ratio of between-class scatter to within-class scatter. Raman spectroscopy was used to distinguish between normal tissue, low-grade dysplasia, and high-grade dysplasia/carcinoma in situ using rat models. A specificity of 93% and sensitivity of 78% were obtained for detecting low-grade dysplasia, and a sensitivity and specificity of 100% was obtained for detecting high-grade dysplasia/carcinoma in situ. Fluorescence spectroscopy was applied in order to detect cancer in the oral cavity. The results were of a sensitivity of 73% and specificity of 92%, after selecting features using recursive feature elimination (RFE).

Reflectance and fluorescence spectroscopy, respectively, have been used to differentiate normal and precancerous (neoplastic) cervical tissue using a Mahalanobis distance classifier. A sensitivity of 72% and specificity of 81% were reported when discriminating between squamous normal tissue and high-grade squamous intraepithelial lesions, while a sensitivity of 72% and a specificity of 83% were obtained when discriminating columnar normal tissue from high-grade squamous intraepithelial lesions. An average sensitivity and specificity of 78% and 81% respectively were obtained when the pairwise analysis between squamous normal tissue, columnar normal tissue, low-grade squamous intraepithelial lesions and high-grade squamous intraepithelial lesions was done.

Another method being applied to spectroscopy data is artificial neural networks (ANN). These are typically known for being able to handle nonlinear problems. As an example of their use, an ANN classifier was used for distinguishing malignant melanoma from benign nevi in the skin using reflectance spectra, with a classification accuracy of 86.7% being reported. ANN yielded sensitivities of 69% and 58%, and specificities of 85% and 93%, for breast tissue and sentinel nodes, respectively, using data from elastic-scattering spectroscopy measurements.

In recent years, support vector machines (SVM) have received increased attention in these types of applications. This is in part due to the fact that SVMs exhibit good generalization capability and are able to yield nonlinear decision boundaries through the implicit mapping of the data to a higher dimensional space by the use of kernel functions. Linear SVMs were used to classify nonmalignant and malignant tissue from the breast measured with fluorescence spectroscopy, obtaining a sensitivity of 70% and specificity of 92%. SVMs with linear and radial basis function (RBF) kernels have also been used. Sensitivities of 94% and 95%, and specificities of 97% and 99%, respectively, were obtained for distinguishing normal tissue from nasopharyngeal carcinoma using autofluorescence spectra. Fluorescence spectroscopy has been applied in order to detect cancer in the oral cavity. The results were of a sensitivity of 88%, 90%, 93% and specificity of 94%, 95%, 97%, for linear, polynomial, and RFB SVMs respectively, after selecting features using recursive feature elimination (RFE).

As support vector machines (SVMs) have garnered increased attention for classification problems, several error-rejection rules have been presented for this type of classifier. For points near the optimal hyperplane the classifier may not be very confident in the class labels assigned. In these prior approaches, a rejection scheme was proposed in which samples whose distance to the separating hyperplane is below some threshold are rejected. A similar approach was used where the distance of tested data points to the optimal separating hyperplane was thresholded in order to reject a user-defined percentage of miss-classified patterns, allowing for the reduction of the expected risk. A ROC-based reject rule has been proposed for SVMs. The ROC curve for the SVM classifier is obtained by varying the decision threshold, which is assumed to be zero, from $-\infty$ to $\infty$. The true positive and false positive rates are obtained from the class-conditional densities produced by the outputs of the SVMs. A distance reject threshold has also been presented for SVM classifiers. The SVM output is the distance of that particular input pattern to the optimal separating hyperplane.

The foundation of these error rejection rules can be traced to the work presented by Chow. These error rejection rules are disadvantageous because they assume that the probability distribution for each class is known. In most pattern recognition applications common parametric forms rarely fit the densities encountered in practice.

Chow first explored error rejection in the context of Bayes decision theory. Within this framework, a feature vector x is said to belong to class $w_k$ if $$P(w_k/x) = \max_i P(w_i/x), \qquad (1)$$

$$i = 1, \ldots, N$$

where $P(w_i/x)$ is the a posteriori probability and N is the total number of classes. This rule divides the feature space into N regions $D_1 \ldots D_N$ and classifies x as $w_k$ if it lies in the region $D_k$. Furthermore, it is optimal in the sense that it minimizes the probability of error, also called the Bayes error, $$P_E = \sum_{i=1}^{N} \int_{D_i} \sum_{\substack{j=1 \\ j \neq i}}^{N} p(x/w_j) P(w_j) dx. \qquad (2)$$

Chow introduces the reject option in order to obtain a probability of error lower than the Bayes error. This is accomplished by refraining from classifying patterns that are likely to be misclassified. Chow's rule states that a feature vector x is classified as belonging to class $w_k$ if $$\max_{i=1,\ldots,N} P(w_i/x) = P(w_k/x) \geq t \qquad (3)$$

and rejected if $$\max_{i=1,\ldots,N} P(w_i/x) = P(w_k/x) < t \qquad (4)$$

where t is the rejection threshold. Thus, the introduction of the reject option divides the feature space into N+1 decision regions $D_0, D_1, \ldots, D_N$ and classifies x as $w_k$ if it lies in the region $D_k$ and rejects it if it lies in $D_0$. It is optimal since $P(w_k/x)$ is the conditional probability of correctly classifying the pattern x. Note that both the probability of error (2) and the probability of rejection $$P_R = \int_{D_0} \sum_{i=1}^{N} p(x/w_i) P(w_i) dx \qquad (5)$$

are now functions of the threshold t. Chow states that since (2) and (5) are monotonic functions of the threshold t, the performance of the recognition system is completely described by the curve resulting from (2) versus (5). In this error-reject tradeoff curve $P_E$ decreases and $P_R$ increases as the threshold t increases. In particular, $P_E$ equals the Bayes error and $P_R=0$ for t=0, and $P_E=0$ for t=1. A similar relationship was presented between false acceptance rates and false rejection rates as a function of the rejection threshold in the application of biometric verification systems.

Another rejection scheme was proposed to improve reliability in neural networks. It defines two classification rules and finds a threshold for each. Let $O_k$ be the output node corresponding to class k, if the input samples corresponds to the kth class then the output node $O_k=1$ while all other equal zero. The first rule states that an input pattern belongs to class k if $$\max_{i=1,\ldots,N} O_i = O_k \geq \sigma \qquad (6)$$

where $\sigma$ is the rejection threshold, similar to Chow's rule. The second rule states that $$O_k - O_j < \delta \qquad (7)$$

where $O_j$ is the output node with the second highest value and $\delta$ is the rejection threshold. Thus, if the difference between the two highest output values is less than some threshold the input pattern is not classified. The two thresholds are then obtained by maximizing a performance function that depends on the error and rejection rates as well as their respective costs.

The optimality of Chow's rule has also been investigated. Some say that Chow's rule is optimal only if the posterior probabilities of the data classes are exactly known; however, it is generally not the case and posterior probabilities have to be estimated from the training data. As a result, sub-optimal results are obtained when this rule is applied to the estimated probabilities since the decision regions are shifted with respect to where they would be in the optimal case. The use of multiple class dependent thresholds has been proposed as a solution. In this approach Chow's rule is modified, a pattern x is classified as belonging to class $w_k$ if $$\max_{i=1,\ldots,N} \hat{P}(w_i/x) = \hat{P}(w_k/x) \geq t_k \qquad (8)$$

and rejected if $$\max_{i=1,\ldots,N} \hat{P}(w_i/x) = \hat{P}(w_k/x) < t_k. \qquad (9)$$

Here $\hat{P}(w_i/x)$ is the estimated posterior probability. The thresholds are determined by maximizing the accuracy probability subject to maintaining the reject probability below a user defined value. Both the accuracy and reject probabilities are function of the class thresholds.

Another rejection rule was based on analysis of the Receiver Operating Characteristic (ROC) curve. The two classes are called Positive (P) and Negative (N) and the decision rule is defined as:
assign the sample to N if $x < t_N$
assign the sample to P if $x > t_P$
reject the sample if $t_N \leq x \leq t_P$
where $t_N$ and $t_P$ ($t_N \leq t_P$) are the rejection thresholds. The optimal thresholds maximize a performance function defined by the false negative, true negative, false positive, true positive and rejection rates, respective costs and prior probabilities. The solution yields a set of parallel straight lines whose slopes are determined by the costs and prior probabilities. The optimal values for the thresholds are then found by searching the point on the ROC curve, constructed by graphing the true positive rate versus false positive rate, which intersect these lines and have minimum value.

Another rejection rule that has been considered deals with incomplete knowledge about classes. In this work two rejection thresholds were defined. The first, the ambiguity reject threshold, like Chow's rule aims to reject samples with high risk of misclassification in order to decrease the classification error. The second, denoted distance reject threshold, aims to decrease the probability of erroneously classifying an input pattern x into one of the N classes when it is "far" from the known classes (i.e. outliers). The assumption is that not all patterns come from one of the N previously defined classes. This same rejection rule was applied to neural networks classifiers. The optimum class-selective rejection rule is presented. This approach is another extension of the rejection rule, when an input pattern cannot be reliably classified as one of the defined N classes, instead of being rejected it is assigned to a subset of classes to which the pattern most likely belongs to. Thus the feature space is divided into $2^N - 1$ decision regions instead of N+1 regions as in Chow's rule.

Even though these methods cover a wide range of applications using different spectroscopy methods and several types of classifiers, the sensitivities and specificities obtained do not vary much for each of the cases presented. With few exceptions, the average sensitivity and specificity fluctuates between 70% and 85%.

Thus, what is needed is an improved method for classifying optical spectroscopy data. These improved methods can be used to improve diagnosis and, therefore, treatment of cancer and other pathologies.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

According to an aspect of the invention, a method is provided for classifying a tissue sample that includes training a classifier to determine a rejection region of biomedical spectra data corresponding to tissue samples that are likely to be misclassified; classifying the tissue sample if biomedical spectra data corresponding to the tissue sample is not in the rejection region; and withholding from classifying the tissue sample if the biomedical spectra data corresponding to the tissue sample is in the rejection region.

The method may also include performing a biopsy of the tissue sample if the classification is withheld.

The method may also include performing additional optical measurements of the tissue sample if the classification is withheld.

Training the classifier may include formulating a training problem as a convex optimization problem dual training algorithm.

The biomedical spectra data may be ESS data.

According to another aspect of the invention, a method for classifying a tissue sample is disclosed that includes classifying a first region of biomedical spectra data using a first classifier; classifying a second region of biomedical spectra data using a second classifier, the first region being different than the second region; and combining the classification of the first classifier with the classification of the second classifier to determine a classification of the tissue sample.

The biomedical spectra data may be ESS data.

The classification of the first classifier and the classification of the second classifier may be selected from the group consisting of positive, negative and rejected.

The first region may overlap the second region.

The method may also include classifying a third region of the biomedical spectra data using a third classifier and classification of the third classifier may be combined with the classification of the first classifier and the classification of the second classifier to determine the classification of the tissue sample.

Classifying the first region may include withholding from classifying the first region. Classifying the second region may include withholding from classifying the second region.

The first classifier and the second classifier may be support vector machines. The first classifier and the second classifier may be support vector machines embedded with error rejection.

Combining the classification of the first classifier with the classification of the second classifier may use a majority voting rule. Combining the classification of the first classifier with the classification of the second classifier may use a naive Bayes rule.

According to a further aspect of the invention, a machine readable storage medium comprising instructions executable by a data processing machine is disclosed to perform the methods disclosed herein. According to additional aspects of the invention, a computer system is disclosed including memory and a processor configured to perform the method steps disclosed herein and a computer system is disclosed including means for performing the method steps disclosed herein.

According to another aspect of the invention, a system configured to classify a tissue sample is disclosed that includes an optical probe configured to measure the biomedical spectra data; and a classification system coupled to the optical probe comprising a support vector machine with embedded error rejection to classify the biomedical spectra data.

The optical probe may be an integrated biopsy forceps tool. The integrated biopsy forceps tool may include an illuminating optical fiber to direct light at tissue to be imaged and a collecting optical fiber to collect the light scattered in the tissue. The biomedical spectra data may be ESS data.

The classification system may include a plurality of support vector machines with embedded error rejection to classify the biomedical spectra data. Each of the plurality of support vector machines with embedded error rejection is configured to classify a different region of the spectra data. The classification system may combine the outcome of each of the plurality of support vector machines with embedded error rejection to make a final classification of the biomedical spectra data.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

FIG. 1A illustrates an optical geometry of a fiber probe used for ESS.

FIG. 1B illustrates a fiber probe detection system.

FIG. 2A illustrates an integrated biopsy forceps.

FIG. 2B illustrates an integrated biopsy forceps.

FIG. 4 illustrates a SFFS algorithm.

FIG. 5 illustrates a SVDSS algorithm.

FIG. 9 illustrates a process to analytically optimize two lagrange multipliers.

FIG. 10 illustrates KKT violations.

FIG. 14 illustrates an AdaBoost training algorithm.

DETAILED DESCRIPTION

Figure 3:
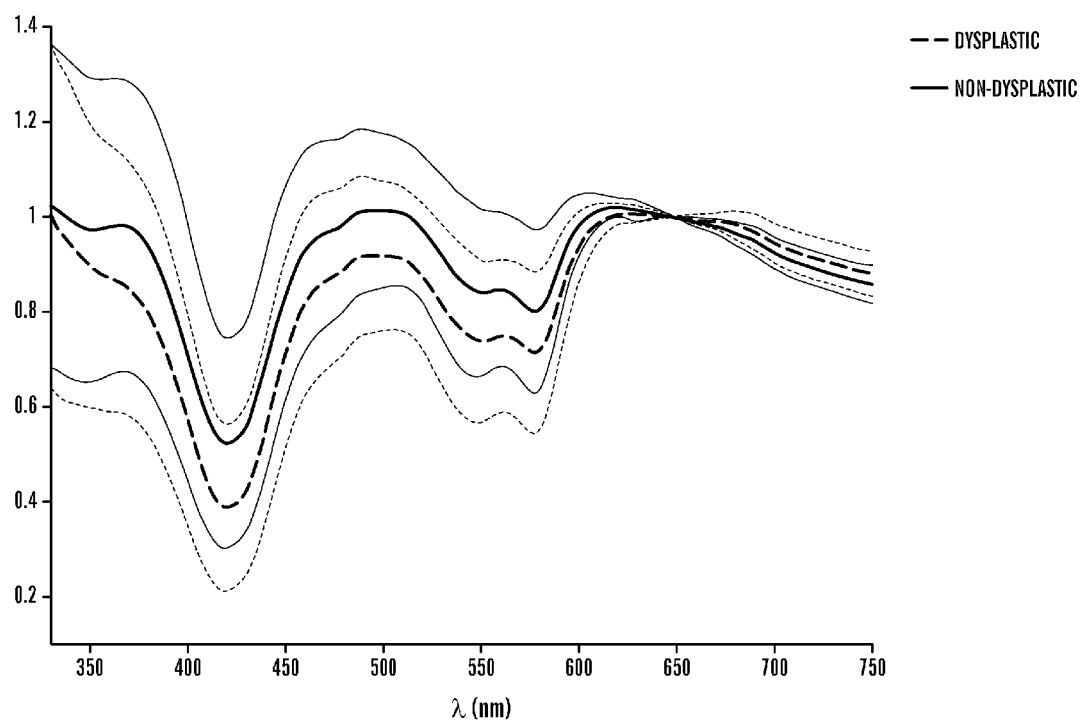
FIG. 3 illustrates exemplary measured ESS spectra for normal and cancerous tissue.

Various types of optical spectroscopy, in general, including elastic-scattering spectroscopy (ESS), provide a minimally invasive approach for obtaining spectral measurements of the scattering properties of tissue. These techniques allow for the acquisition of spectral signatures of the underlying tissue, for the purpose of sensing pathologies including, for example, cancer. The ESS method is sensitive to the wavelength dependence of the tissue optical scattering properties, which vary due to architectural changes at the cellular and sub-cellular level as a result of the different pathologies. These changes influence the measured spectral signatures, with spectral variations that depend on the pathology.

Embodiments of the present invention make use of mathematical/statistical pattern-recognition systems, with novel approaches in implementation, to distinguish between different pathologies and benign conditions (e.g., normal or cancerous tissue) given the spectra measured using optical spectroscopy, such as EES. In embodiments of the present invention, a given spectrum may be specified as normal or cancerous, but may also not be classified (i.e., rejected). Samples that are not classified (i.e., rejected) include samples with a high risk of misclassification (i.e., samples lying close to the decision boundary within certain thresholds). The training algorithm is reformulated for each of the classifiers to optimally determine the decision boundary and these thresholds without significantly changing the classifier's original structure.

Embodiments of the present invention are directed to multiple classifier systems that makes a final diagnostic decision based on the classification of each of the individual classifiers. Each of the individual classifiers may be designed to use features extracted from a limited region of the ESS spectrum. Each of the individual classifiers may also be SVM classifiers embedded with error rejection. In particular, the training algorithm of these SVM classifiers may be formulated to optimally determine the decision boundary.

FIGS. 1A-1B illustrate an exemplary EES probe 100. The EES probe 100 is used to collect the EES spectra data for analysis. The EES probe 100 is configured to be positioned in optical contact with tissue under examination 104. As shown in FIG. 1A, the EES probe 100 includes an illuminating fiber 108 and a collecting fiber 112. The light 116, provided by a light source 120, is directed at the tissue 104 by the illuminating fiber 108. The light 116 undergoes multiple scattering 124 through a small volume of the tissue being examined. The light 116 is then collected and transmitted by the collecting fiber 112 to the analyzing spectrometer (the detector 128 that is coupled to a computer and interface 132 as shown in FIG. 1B. In one embodiment, the light source 120 is a pulsed Xenon-arc lamp broadband light source and the computer and interface 132 is a portable laptop computer with custom ESS software and built-in spectrometer (e.g., S2000 by Ocean Optics, Inc.)

The resulting effective path length of the collected photons is generally several times greater than the actual separation of the fiber tips. It will be appreciated that the fiber probe examines only the site that is in optical contact with it and does not image the tissue surface.

FIGS. 2A and 2B illustrate an exemplary integrated biopsy forceps 200. The integrated biopsy forceps 200 incorporates an ESS probe 100 into bioposy forceps 204 The forceps 204 include a metal hypotube 208 that includes the optical fibers 108, 112. The hypotube 208 is positioned in a central chamber extending the length of the integrated biopsy forceps, and extends into the space between the jaws 212, 216.

The optical fibers 108, 112 in the integrated biopsy forceps 200 are smaller than conventional optical fibers and closer together than conventional optical fibers. In one embodiment, the separation between the illumination and collection fibers 108, 112 is about 250 µm from center-to-center, and each fiber 108, 112 having a diameter of about 200 µm and a numerical aperture of about 0.22 in air. The diameter of the hypotube 208 was about 0.470 mm. It will be appreciated, however, that the probe geometry may have a different configuration than that described herein.

The probe 100 generates a spectrum that characterizes the wavelength dependences of both scattering and absorption of the underlying tissue, without separating these contributions. FIG. 3 illustrates an exemplary spectrum for colon polyps. In the example shown in FIG. 3, ESS measurements from 280 polyps from 115 patients were measured (98 corresponded to hyperplastic polyps, 85 to normal growths, 10 to inflammatory polyps, 83 to tubular adenomas, 1 to tubular villious adenoma, 2 to adenocarcinoma and 1 to high-grade dysplasia). The data was grouped into non-dysplastic (hyperplastic polyps, normal and inflammatory polyps) and dyplastic polyps (tubular adenoma, tubular villious adenoma, adenocarcinoma and high-grade dysplasia). In FIG. 3, the average spectrum for the non-dysplastic and dysplastic measurements are shown with their standard deviation.

Diagnostic algorithms that are based on pattern recognition methods include (2) pre-processing and feature extraction/selection and (2) classification. These algorithms then undergo (3) performance evaluation to gauge their accuracy.

In pre-processing, the data is prepared for analysis, and typically includes standardization of the data set and/or noise reduction operations (e.g. smoothing of the spectra). In feature extraction/selection, the most relevant information from the data set is obtained in such a way that class separability is preserved or improved as much as possible. This may involve transforming the data to a lower dimensional subspace or selecting a subset of features from the data set based on certain criteria. Feature extraction methods create new features based on transformations of combinations of the original feature set, e.g. Principle Component Analysis (PCA). Feature selection selects the best subset of the input feature set, usually based on some predefined class-separability measure.

In classification, a decision (e.g., normal vs. cancerous, progressions of the disease, etc.) is made about the nature of the input pattern (e.g., the ESS spectra). The importance of avoiding misclassified samples is clear, which in real settings is hard to achieve. To this end, a methodology is described herein that is able to identify samples that are at high risk of being misclassified. By identifying these "rejected" samples, they can then be examined and diagnosed more accurately by other methods.

In performance evaluation, the accuracy of the decisions made by the classifier is determined. The criteria used for evaluation are the sensitivities, specificities and classification error attained with a particular classifier. In some cases the positive and/or negative predictive value is of interest and is also used as an evaluation criteria. When error-rejection is employed as an additional criterion, the percentage of samples not classified, is considered in the performance evaluation.

Embodiments of the invention are directed to systems and methods that perform feature selection using Sequential Floating Forward Selection (SFFS) in the field of biomedical spectroscopy to pre-process the spectra data. SFFS is advantageous because the physical meaning of the features is not lost in the transformation process. The SFFS method is also advantageous because it performs on par with algorithms that obtain optimal solutions, i.e. methods that search all possible subsets, yet demands lower computational resources.

Sequential Floating Forward Selection (SFFS), shown in FIG. 4, sequentially includes the most significant feature at the forward step and, after this step, excludes the least significant in a number of backwards steps as long as the resulting subsets are better than the previously evaluated ones at that level. This avoids the "nesting" of the feature subsets arising from pure Sequential Forward Search methodologies. As shown in FIG. 4, the significance of a feature is determined by the metric J(g), chosen a priori. This is usually chosen to be some class separability measure, e.g. the Bhattacharya distance or the classification error rate.

Principal Component Analysis (PCA) is another method for feature extraction. PCA reduces dimensionality by restricting attention to those directions along which the variance of the data is greatest. These directions are obtained by selecting the eigenvectors of the pooled data covariance matrix that correspond to the largest eigenvalues. Dimensionality reduction is then achieved by applying the linear transformation of the form:

$$x\% = A^T x \tag{0.1}$$

where A is the transformation matrix whose columns contain the desired d eigenvectors and x is the input vector. It is worth noting that although PCA finds components that are useful for representing the data in lower dimensions, there is no guarantee that these components are useful for discrimination between classes. PCA is an unsupervised linear feature extraction method, i.e. no measure of class separability is incorporated while finding the principal components. Also, since PCA reduces dimensionality by way of a linear transformation, the physical meanings of the input vector's features are effectively lost.

An alternate method for feature selection is singular value decomposition subset selection (SVDSS), shown in FIG. 5. While SFFS is a supervised feature selection method, i.e. labeled samples are needed in the algorithm, SVDSS is an unsupervised feature selection method. SVDSS selects the d features that best approximate the first d principal components using heuristic algorithm based on the singular value decomposition, as shown in FIG. 5. Like PCA, while no class separability criterion is used, the SVDSS algorithm exhibits good performance in practical applications.

Figure 6A:
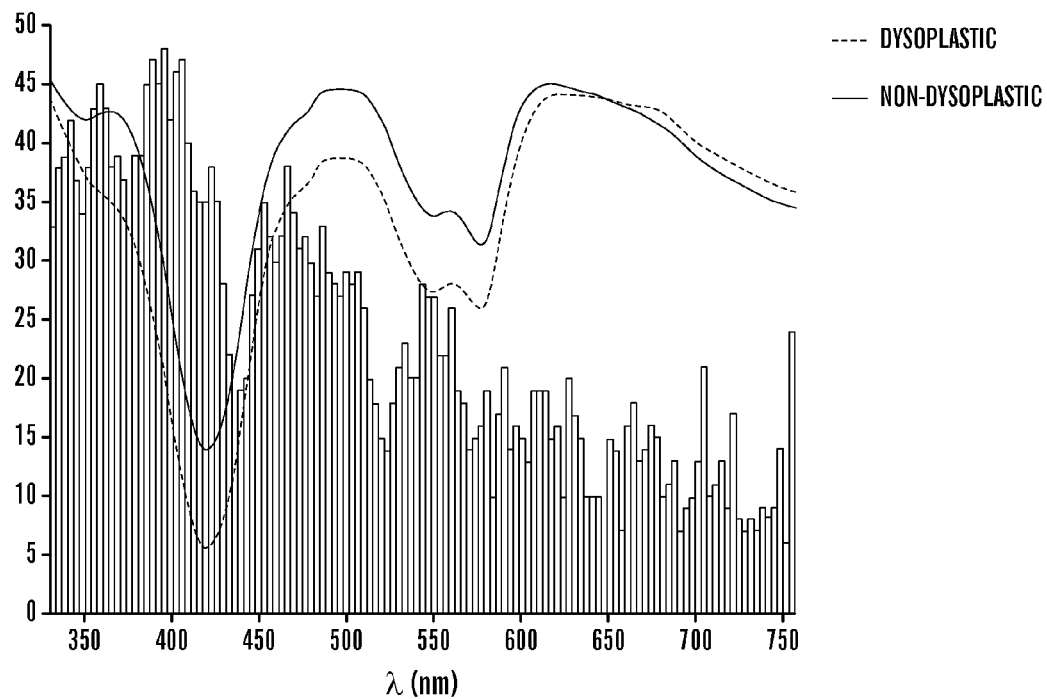
FIGS. 6A and 6B illustrates average spectra and histogram of selected features with SFFS.
Figure 6B:
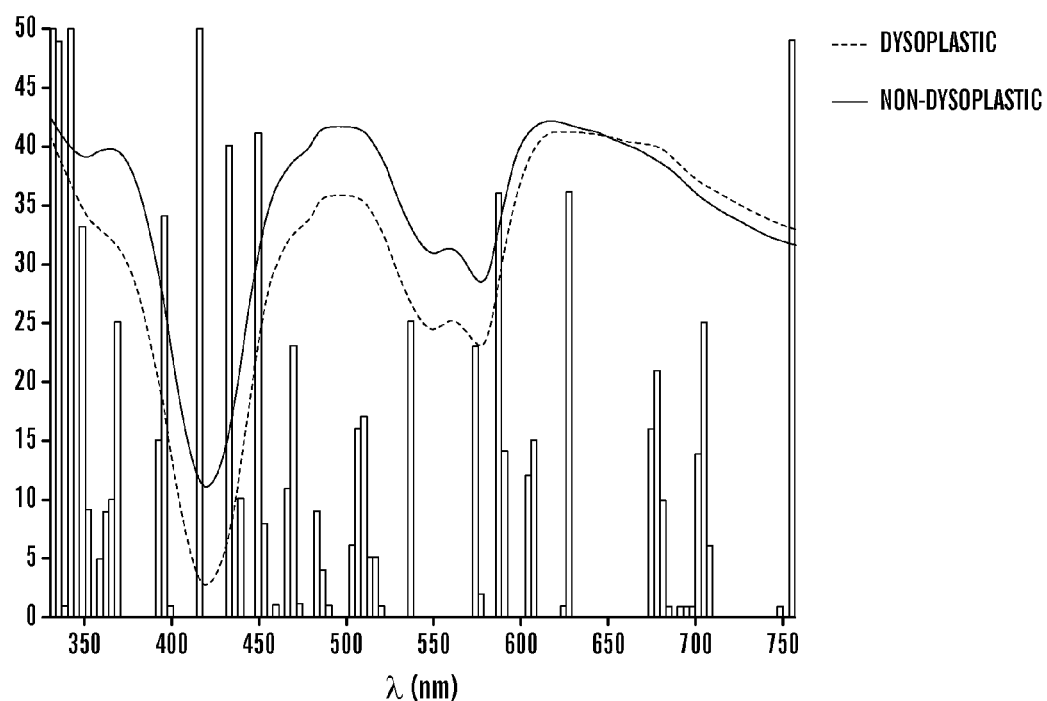

Histograms of the selected features using SFFS and SVDSS are shown in FIGS. 6A and 6B, respectively.

TABLE 1

Results for Feature Extraction/Selection Methods.

| Method | # of Features | Sensitivity | Specificity | Error Rate |
|---|---|---|---|---|
| PCA | 15 | .7417 ± .0757 | .7538 ± .0528 | .2499 ± .0364 |
| SFFS | 58 | .7217 ± .0785 | .7777 ± .0425 | .2396 ± .0323 |
| SVDSS | 17 | .7434 ± .0706 | .7608 ± .0503 | .2446 ± .0351 |

While there is no clear gain in performance, the use of feature selection methods, like SFFS and SVDSS, can help gain an intuition into what parts of the spectrum are more relevant in terms of discriminating non-dysplastic from dysplastic polyps. As shown in FIGS. 6A and 6B, the shorter wavelengths, 330-440 nm, are particularly useful for this task. These experiments led to the use of the 330-760 nm rather than 370-800 nm previously used.

Support vector machines (SVMs) were selected for classification. SVMs are in their simplest forms binary linear classifiers where the decision boundary obtained is a hyperplane that has the maximum separating margin between the classes. Two important properties of this hyperplane include: (1) the separating hyperplane with maximum margin is unique, and (2) this hyperplane can be obtained by solving a quadratic optimization problem.

Let $x_i \in \mathfrak{R}^d$, be an input vector and $y_i \in \{1, -1\}$ its corresponding label for $=1, \ldots, 1$, where l is the total number of training samples. We want to learn the linear classifier of the form:

$$f(x) = \text{sign}(w^T x + b) \quad (10)$$

which provides maximum margin between the classes. Furthermore, we assume that the classes are linearly separable, i.e. a hyperplane can be found which separates the classes without error. If we denote w as the normal to the hyperplane and $|b|/\|w\|$ the perpendicular distance from the hyperplane to the origin, where $\|\cdot\|$ is the 2-norm, then the training points must satisfy the following constraints:

$$w^T x_i + b \geq +1 \text{ for } y_i = +1$$

$$w^T x_i + b \leq -1 \text{ for } y_i = -1. \quad (11)$$

Training points satisfying the equalities in the constraints in (11) lie in two hyperplanes that define the margin between classes, and it can be seen that this margin is $2/\|w\|$. Thus, finding the hyperplane with maximum margin separation can be done by minimizing $\|w\|^2$ subject to the constraints in (11).

An extension of this problem for the case when the data is not separable was presented. The constraints are relaxed to allow errors, and a penalty term was introduced in the cost function. This was accomplished by introducing the positive slack variables $\xi_i$, i=1, . . . , l. The constraints are then modified as follows:

$$w^T x_i + b \geq +1 - \xi_i \text{ for } y_i = +1$$

$$w^T x_i + b \leq -1 + \xi_i \text{ for } y_i = -1$$

$$\xi_i \geq 0 \forall i. \quad (12)$$

The new cost function is then $$\|w\|^2 + C \sum_i \xi_i \quad (13)$$

where C is a pre-defined constant that controls how much penalty is given to errors and is usually selected using cross-validation methods. The summand in (13) can be viewed as an upper bound on the number of training errors, noting that a training error here is defined as patterns where the inequalities in (12) holds with $\xi_i > 0$. Minimizing (13) with constraints (12) constructs a separating hyperplane that minimizes the sum of deviations, $\xi_i$, of training errors and maximizes the margin for samples correctly classified.

Since this is a convex optimization problem with linear constraints, the solution can be attained by solving the equivalent dual problem formulation. By setting the derivatives of the Lagrangian function with respect to the variables w, b and $\xi_i$, to zero and substituting back the following equivalent problem is obtained: maximize $$\sum_i \alpha_i - \frac{1}{2} \sum_{i,j} \alpha_i \alpha_j y_i y_j x_i^T x_j \quad (14)$$

subject to $$\sum_i \alpha_i y_i = 0 \quad (15)$$

$$0 \leq \alpha_i \leq C.$$

From the derivative of the Lagrangian with respect to w an expression is obtained for computing w in terms of the Lagrange multipliers $\alpha_i$:

$$w = \sum_i \alpha_i y_i x_i, \quad \text{for } \alpha_i > 0 \quad (16)$$

From this problem an interesting result can be obtained for the case where the data is separable by a non-linear decision boundary. Noticing that the only way the data appears in this formulation is in the form of the dot products $x^T x$, the data could be mapped to a higher, and possibly infinite dimensional, space using a kernel function $K(x_i, x_j)$. This kernel function in the input space is equivalent to the dot product in that high dimensional space. The only restriction is that this kernel function must satisfy Mercer's conditions. By replacing the dot product, $x^T x$, with the kernel $K(x_i, x_j)$ everywhere in the training algorithm, the algorithm will find a linear decision boundary in the high dimensional space that when mapped back to the input space will be non-linear depending on the kernel. More importantly, this is accomplished by solving the same convex training problem. The decision function is then obtained by:

$$f(x) = \sum_i \alpha_i y_i K(x_i, x) + b, \quad \text{for } \alpha_i > 0. \tag{17}$$

It will be appreciated that the SVM may use any type of kernel. Exemplary kernels include linear kernels, polynomial $2^{nd}$ degree kernels, polynomial $3^{rd}$ degree kernels, polynomial $4^{th}$ degree kernels, RBF kernels and the like. The application of different kernels, and thus decision boundaries, to the problem of classifying ESS spectra from non-dysplastic and dysplastic polyps is a classification problem that is not only linearly non-separable but also nonlinearly non-separable. Thus, the radial basis function (RBF) kernel may be advantageous over the linear kernel and the polynomial kernels.

Support Vector Machines with Embedded Error-Rejection

Embodiments of the invention are directed to a SVM training problem with embedded error-rejection that remain a convex optimization problem. This enables retention of the global solution present in the original SVM formulation. In addition, a convex optimization problem facilitates the development of a dual algorithm where there is no duality gap.

The training problem for SVM with embedded error rejection involves finding a decision region defined by a pair of parallel hyperplanes $$w^T x - b + \epsilon = 0 \tag{18}$$

where samples lying in between them would be rejected and, in keeping with the original SVM training problem, the samples correctly classified should be separated with maximum margin. In other words, the classifier has the following decision function $$f(x) = \begin{cases} +1 & \text{if } w^T x - b \geq \epsilon \\ -1 & \text{if } w^T x - b \leq -\epsilon \\ 0, & \text{if } -\epsilon < w^T x - b < \epsilon \end{cases} \tag{19}$$

where, w is the normal to the hyperplane, $|b|/\|w\|$ is the perpendicular distance of the hyperplane to the origin, and $2\epsilon/\|w\|$ is the distance between the parallel hyperplanes that define the rejection region. By constraining $0 \leq \epsilon \leq 1$, the rejection region lies inside the margin $2/\|w\|$.

Figure 7A:
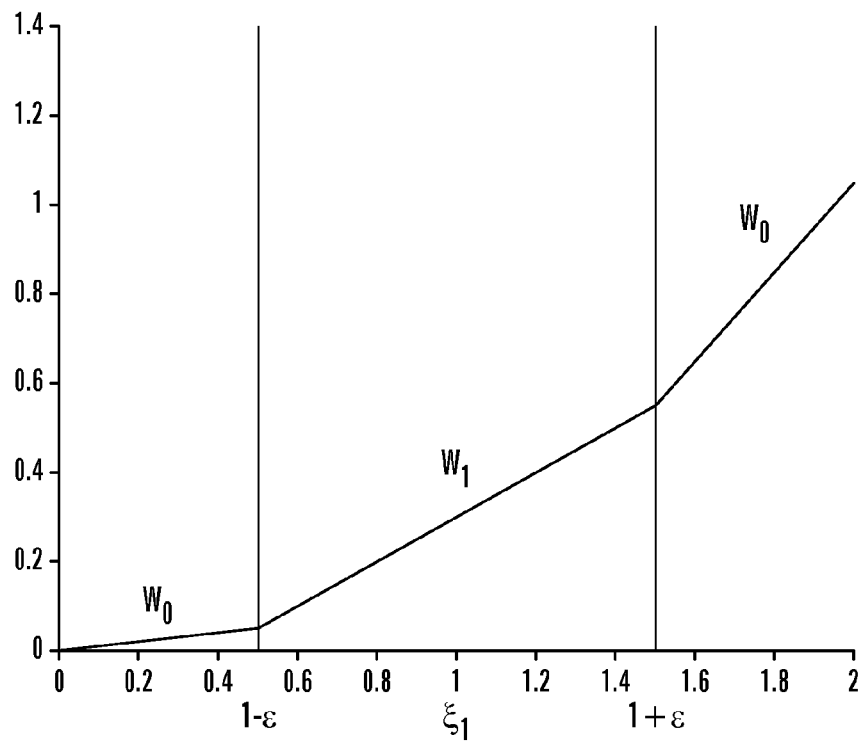
FIG. 7A illustrates behavior of function $h(\xi_i, \epsilon)$.

A new functional, $h_c(\xi_i, \epsilon)$ is introduced, which is defined as:

$$h_c(\xi_i, \epsilon) = \max \begin{pmatrix} w_c \xi_i, \\ w_r \xi_i + (w_r + w_c)\epsilon + w_c - w_r, \\ w_e \xi_i + (2w_r - w_c - w_e)\epsilon + w_c - w_e \end{pmatrix} \tag{20}$$

with $0 < w_c < w_r < w_e$, where $w_c$ is the cost assigned to samples correctly classified but with $0 < \xi_i \leq 1 - \epsilon$, i.e. correctly classified samples lying inside the margin, $w_r$ is the reject cost assigned to samples that satisfy $1 - \epsilon \leq \xi_i \leq 1 + \epsilon$, the rejected samples lying inside the rejection region, and $w_e$ is the cost of misclassified samples satisfying $1 + \epsilon < \xi_i \leq w_e$. $\xi_i \geq 0$ are the deviations from the training errors. FIG. 7A shows the behavior of the function $h_c(\xi_i, \epsilon)$.

To find the optimal decision region that maximizes the margin while accounting for the tradeoff between rejecting and misclassifying samples the following training problem is posed for a SVM with embedded error-rejection:

$$\min_{w,b,\xi_i,\epsilon} \frac{1}{2} w^T w + C \sum_i h_c(\xi_i, \epsilon) \tag{21}$$

$$\text{s.t.} \quad y_i(w^T x_i + b) \geq 1 - \xi_i$$

$$\xi_i \geq 0$$

$$0 \leq \epsilon \leq 1,$$

where $y_i = \{-1, 1\}$ is the label of the training sample $x_i$, and $C > 0$ is the cost assigned to the errors. Thus, the solution of this problem constructs two separating hyperplanes of width $2\epsilon/\|w\|$ between them, that minimizes the sum of deviations, $\xi_i$, of training errors weighted by $w_c$, $w_r$, and $w_e$ while maximizing the margin, $2/\|w\|$, for samples correctly classified. In addition, the solution is global since a convex optimization problem with linear constrains is solved given that the functional $h_c(\xi_i, \epsilon)$ is a convex function.

The fact that $h_c(\xi_i, \epsilon)$ is a piecewise convex function allows formulation of the following equivalent problem of the one presented in (21):

$$\min_{w,b,\xi_i,\epsilon,z_i} \frac{1}{2} w^T w + \sum_i z_i \tag{22}$$

$$\text{s.t.} \quad y_i(w^T x_i - b) \geq 1 - \xi_i$$

$$z_i \geq C w_c \xi_i$$

$$z_i \geq C[w_r \xi_i + (w_r - w_c)\epsilon + w_c - w_r]$$

$$z_i \geq C[w_e \xi_i + (2w_r - w_c - w_e)\epsilon + w_c - w_e]$$

$$\xi_i \geq 0$$

$$0 \leq \epsilon \leq 1.$$

The goal now is to obtain the dual formulation of problem in (22) (primal formulation), allowing for construction of nonlinear decision boundaries using the kernel function $K(x_i, x_j)$. Nonlinear rejection regions are obtained by solving the dual of the problem presented in (22). First, the Karush-Kuhn-Tucker (KKT) conditions of problem (22) were derived. These consist of the feasibility, optimality and complementary slackness conditions. Feasibility conditions are the constraints stated in (22). The Lagrangian is given by:

$$L = 1/2 w^T w + \sum_i z_i - \sum_i \alpha_i y_i w^T x_i + \sum_i \alpha_i y_i b + \tag{23}$$

$$\sum_i \alpha_i - \sum_i \alpha_i \xi_i - \sum_i \beta c_i z_i + \sum_i \beta c_i C w_c \xi_i -$$

$$\sum_i \beta r_i z_i + \sum_i \beta r_i C w_r \xi_i + \sum_i \beta r_i C(w_r - w_c)\epsilon +$$

$$\sum_i \beta r_i C(w_c - w_r) - \sum_i \beta e_i z_i + \sum_i \beta e_i C w_e \xi_i +$$

-continued
$$\sum_i \beta e_i C(2w_r - w_c - w_e)\varepsilon + \sum_i \beta e_i C(w_c - w_e) - \sum_i \mu_i \xi_i.$$

Differentiating the Lagrangian with respect to the primal variables, the w, b, $\xi_i$, $\epsilon$, $z_i$, the following optimality conditions are obtained:

$$\frac{\partial L}{\partial w} = w - \sum_i \alpha_i y_i x_i = 0 \quad (24)$$

$$\frac{\partial L}{\partial b} = \sum_i \alpha_i y_i = 0 \quad (25)$$

$$\frac{\partial L}{\partial \xi_i} = -\alpha_i + Cw_c \beta c_i + Cw_r \beta r_i + Cw_e \beta e_i - \mu_i = 0 \quad (26)$$

$$\frac{\partial L}{\partial \varepsilon} = C(w_r - w_c)\sum_i \beta r_i + C(2w_r - w_c - w_e)\sum_i \beta e_i = 0 \quad (27)$$

$$\frac{\partial L}{\partial z_i} = 1 - \beta c_i - \beta r_i - \beta e_i = 0. \quad (28)$$

Finally, the complementary slackness conditions are given by:

$$\alpha_i[y_i(w^T x_i - b) - 1 + \xi_i] = 0 \quad (29)$$

$$\beta c_i[z_i - Cw_c \xi_i] = 0 \quad (30)$$

$$\beta r_i[z_i - C(w_r \xi_i + (w_r - w_c)\epsilon + w_c - w_r)] = 0 \quad (31)$$

$$\beta e_i[z_i - C(w_e \xi_i + (2w_r - w_c - w_e)\epsilon + w_c - w_e)] = 0 \quad (32)$$

$$\mu_i \xi_i = 0. \quad (33)$$

To formulate the dual problem the Lagrangian (23) is maximized with respect to the dual variables, $\alpha_i$, $\beta c_i$, $\beta r_i$, $\beta e_i$, $\mu_i$, subject to the constraints that the gradient of the Lagrangian with respect to the primal variables, w, b, $\xi_i$, $\epsilon$, $z_i$, vanishes (Eq. (24)-(28)). After some manipulations the following dual problem is obtained:

$$\max_{\alpha_i, \beta c_i, \beta r_i, \beta e_i} \sum_i \alpha_i - \frac{1}{2}\sum_i \sum_j \alpha_i \alpha_j y_i y_j x_i^T x_j + \quad (34)$$
$$C(w_c - w_r)\sum_i \beta r_i + C(w_c - w_e)\sum_i \beta e_i$$

s.t. $\sum_i \alpha_i y_i = 0$ $\beta c_i + \beta r_i + \beta e_i = 1$ $C(w_r - w_c)\sum_i \beta r_i + C(2w_r - w_c - w_e)\sum_i \beta e_i = 0$ $0 \le \alpha_i \le Cw_c \beta c_i + Cw_r \beta r_i + Cw_e \beta e_i$ $\beta c_i, \beta r_i, \beta e_i \ge 0.$ The above problem is a concave optimization problem and since the primal is convex too, no duality gap exists for the optimal primal and dual solutions. The data only appears in the dual problem (34) in the form of the dot product $x_i^T x_j$, thus nonlinear decision regions will be obtained if a kernel $K(x_i, x_j)$ is used instead. The width of the rejection region is determined by the weights $0 < w_c < w_r < w_e$.

The value of the primal variables w, b, $\epsilon$ from the optimal dual variables is computed in order to obtain the decision function $$f(x) = \begin{cases} +1 & \text{if } \sum_i \alpha_i y_i K(x_i, x) - b \ge \varepsilon \\ -1 & \text{if } \sum_i \alpha_i y_i K(x_i, x) - b \le -\varepsilon \\ 0, & \text{if } -\varepsilon < \sum_i \alpha_i y_i K(x_i, x) - b < \varepsilon. \end{cases} \quad (35)$$

The value of w is obtained from the optimality condition in Eq. (24) as follows:

$$w = \sum_i \alpha_i y_i x_i, \quad \alpha_i > 0. \quad (36)$$

Noting that for a sample $x_i$ whose corresponding dual variable $\alpha_i^*$ has values $0 < \alpha_i^* < Cw_c$ the primal variable $\xi_i^* = 0$ since $\mu_i = Cw_c - \alpha_i > 0$, the complementary slackness condition in Eq. (29) is used to obtain the value of b as follows:

$$b = \sum_j \alpha_j y_j K(x_j, x_i) - y_i, \quad 0 < \alpha_i < Cw_c \quad (37)$$

It is better numerically to compute b as the average of all the points i that satisfy the above condition. The width of the decision region, $\epsilon$, can be obtained in a similar way by observing that for $Cw_c < \alpha_i^* < Cw_r$, $\xi_i^* = 1 - \epsilon$ and for $Cw_r < \alpha_i^* < Cw_e$, $\xi_i^* = 1 + \epsilon$. Again using Eq. (29), $\epsilon$ is computed as:

$$\varepsilon = y_i\left(\sum_j \alpha_j y_j K(x_j, x_i) - b\right), \quad Cw_c < \alpha_i < Cw_r \quad (38)$$

$$\varepsilon = -y_i\left(\sum_j \alpha_j y_j K(x_j, x_i) - b\right), \quad Cw_r < \alpha_i < Cw_e \quad (39)$$

As with the computation of b, $\epsilon$ is obtained with the average of all points i that satisfy these two conditions.

One advantage of formulating the SVM with an embedded error-rejection training algorithm as a convex optimization problem is the fact that there is no duality gap between the primal and dual solution. One such dual training algorithm is Sequential Minimal Optimization (SMO). This algorithm solves the large quadratic programming optimization problem required by SVM training by breaking it into a series of smaller problems. The smallest possible problem involves two Lagrange multipliers. At each step, two Lagrange multipliers are chosen and jointly optimized. Optimality is determined by satisfying the KKT conditions. The SVM is then updated to reflect the optimal values. The main advantage of this algorithm lies in that these smaller problems can be solved analytically, avoiding numerical quadratic programming optimization as an inner loop.

A training algorithm for SVMs with error-rejection based on extensions of SMO (SMOER) is disclosed, noting that this problem is now posed as a convex optimization problem by the introduction of the functional in (20). This is advantages because the KKT conditions are sufficient and necessary for optimality, in addition to a global solution and no duality gap.

Assume $\epsilon$ is kept constant in (21). Then, the dual of (21) for a fixed $\epsilon$ becomes:

$$\max_{\alpha_i} \sum_i \alpha_i - \frac{1}{2}\sum_i \sum_j \alpha_i \alpha_j y_i y_j x_i^T x_j + \min_{\xi_i \geq 0} C \sum_i h_c(\xi_i, \varepsilon) - \alpha_i \xi_i \quad (40)$$

$$\text{s.t.} \quad \sum_i \alpha_i y_i = 0$$

$$0 \leq \alpha_i \leq Cw_e.$$

The term $g(\alpha_i, \epsilon)$, where $$g(\alpha_i, \varepsilon) = \min_{\xi_i \geq 0} C \sum_i h_c(\xi_i, \varepsilon) - \alpha_i \xi_i, \quad (41)$$

is the concave conjugate of $h_c(\xi_i, \epsilon)$. Furthermore, minimizing $g(\alpha_i, \epsilon)$ with respect to $\xi_i$ results in the expression:

$$g(\alpha_i, \varepsilon) = \begin{cases} 0, & 0 \leq \alpha_i \leq Cw_c \\ Cw_c(1-\varepsilon) - \alpha_i(1-\varepsilon), & Cw_c < \alpha_i \leq Cw_r \\ Cw_r(1+\varepsilon) + C(w_c - w_r)(1-\varepsilon) - \alpha_i(1+\varepsilon), & Cw_r < \alpha_i \leq Cw_e, \end{cases} \quad (42)$$

or similarly $$g(\alpha_i, \varepsilon) = \min \begin{bmatrix} 0, \\ Cw_c(1-\varepsilon) - \alpha_i(1-\varepsilon), \\ Cw_r(1+\varepsilon) + C(w_c - w_r)(1-\varepsilon) - \alpha_i(1+\varepsilon), \end{bmatrix}. \quad (43)$$

Figure 7B:
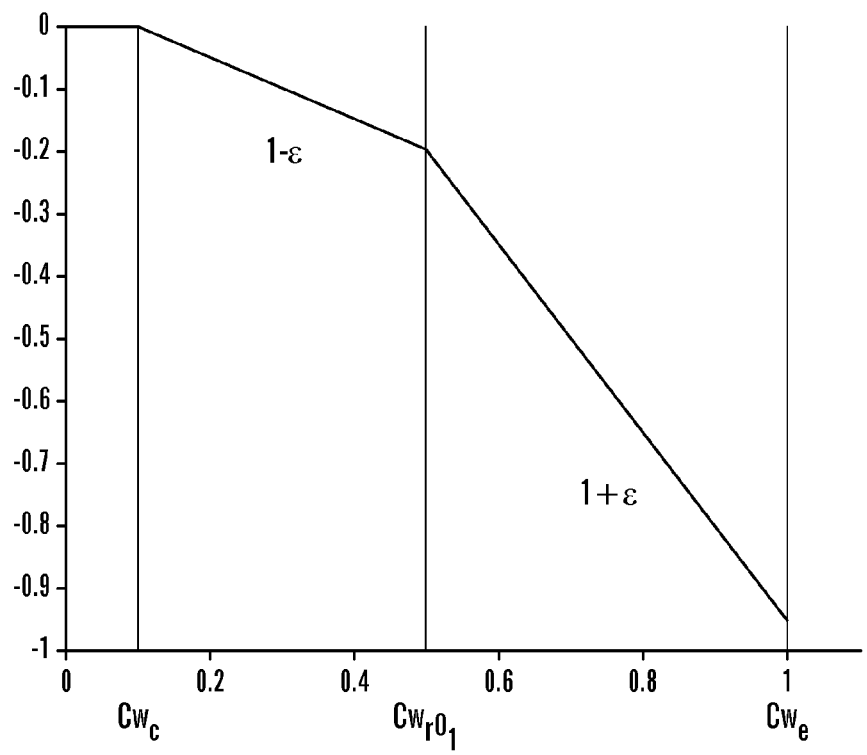
FIG. 7B illustrates behavior of function $g(\alpha_i, \epsilon)$

FIG. 7B illustrates the behavior of $g(\alpha_i, \epsilon)$. Finally, by substituting $g(\alpha_i, \epsilon)$ back in (40) the following dual problem is obtained:

$$\max_{\alpha_i} \sum_i \alpha_i - \frac{1}{2}\sum_i \sum_j \alpha_i \alpha_j y_i y_j x_i^T x_j + \sum_i g(\alpha_i, \varepsilon) \quad (44)$$

$$\text{s.t.} \quad \sum_i \alpha_i y_i = 0$$

$$0 \leq \alpha_i \leq Cw_e$$

The dual problem as stated in (44) is the starting point for the development of the SMO algorithm to train SVM with embedded error-rejection. At every step, the SMO chooses two Lagrange multipliers to jointly optimize, finds the optimal values for these multipliers, and updates the SVM to reflect the new optimal values. This is advantageous because the solving for two Lagrange multipliers can be done analytically, avoiding any numerical QP optimizations. Optimization of the dual variables for the SVM with embedded error-rejection includes three features: analytically solving for the two Lagrange multipliers, a heuristic for choosing which multipliers to optimize, and a method for computing the threshold b.

As described above, the SMO selects two Lagrange multipliers to optimize analytically. For simplicity, all variables that refer to the first and second multiplier will have the subscript 1 and 2 respectively. Optimization of these two multipliers is done within the equality and bound constraints in problem (44). The bound constraint causes the multipliers to lie within a box, while the linear constraint causes the multipliers to lie along the diagonal line, $$\alpha_1 + s\alpha_2 = \gamma, \quad (45)$$

where $s = y_1 y_2$ and $\gamma = \alpha_1^{old} + s\alpha_2^{old}$. The ends of the diagonal line segment when the labels of $\alpha_1$ and $\alpha_2$ are not equal ($y_1 \neq y_2$) are expressed as:

$$L = \max(0, \alpha_2^{old} - \alpha_1^{old})$$

$$H = \min(Cw_e, Cw_e + \alpha_2^{old} - \alpha_1^{old}), \quad (46)$$

and for the case when the labels of $\alpha_1$ and $\alpha_2$ are equal ($y_1 = y_2$) as:

$$L = \max(0, \alpha_1^{old} + \alpha_2^{old} - Cw_e)$$

$$H = \min(Cw_e, \alpha_1^{old} + \alpha_2^{old}). \quad (47)$$

The problem in (44) has to be formulated in terms of $\alpha_1$ and $\alpha_2$ in order to analytically solve for these two dual variables. Using the expression in (45) from the linear constraint and after some manipulations the following unconstrained piecewise concave objective function is obtained:

$$\tfrac{1}{2}\eta\alpha_2^2 + (y_2(E_1^{old} - E_2^{old}) - \eta\alpha_2^{old})\alpha_2 + g(\alpha_2, \epsilon) + g(\gamma - s\alpha_2, \epsilon) + \text{const.} \quad (48)$$

where $E_i = f^{old}(x_i) - y_i$ is the error on the ith training sample. Differentiating with respect to $\alpha_2$ and equating to zero results in $$\alpha_2 = \alpha_2^{old} - \frac{1}{\eta}\left(y_2(E_1 - E_2) + \frac{\partial}{\partial \alpha_2}g(\alpha_2, \varepsilon) - s\frac{\partial}{\partial \alpha_1}g(\alpha_1, \varepsilon)\right), \quad (49)$$

using the fact that $$\frac{\partial}{\partial \alpha_2}g(\gamma - s\alpha_2, \varepsilon) = -s\frac{\partial}{\partial \alpha_1}g(\alpha_1, \varepsilon), \quad (50)$$

where $\eta = 2K(x_1, x_2) - K(x_1, x_1) - K(x_2, x_2)$ and noting that the function $$\frac{\partial}{\partial \alpha_i}g(\alpha_i, \varepsilon)$$

is the subdifferential of $g(\alpha_i, \epsilon)$ and is defined as:

$$\frac{\partial}{\partial \alpha_i}g(\alpha_i, \varepsilon) = \begin{cases} 0, & 0 \leq \alpha_i \leq Cw_c \\ -(1-\varepsilon), & Cw_c < \alpha_i \leq Cw_r \\ -(1+\varepsilon), & Cw_r < \alpha_i \leq Cw_e. \end{cases} \quad (51)$$

Figure 8:
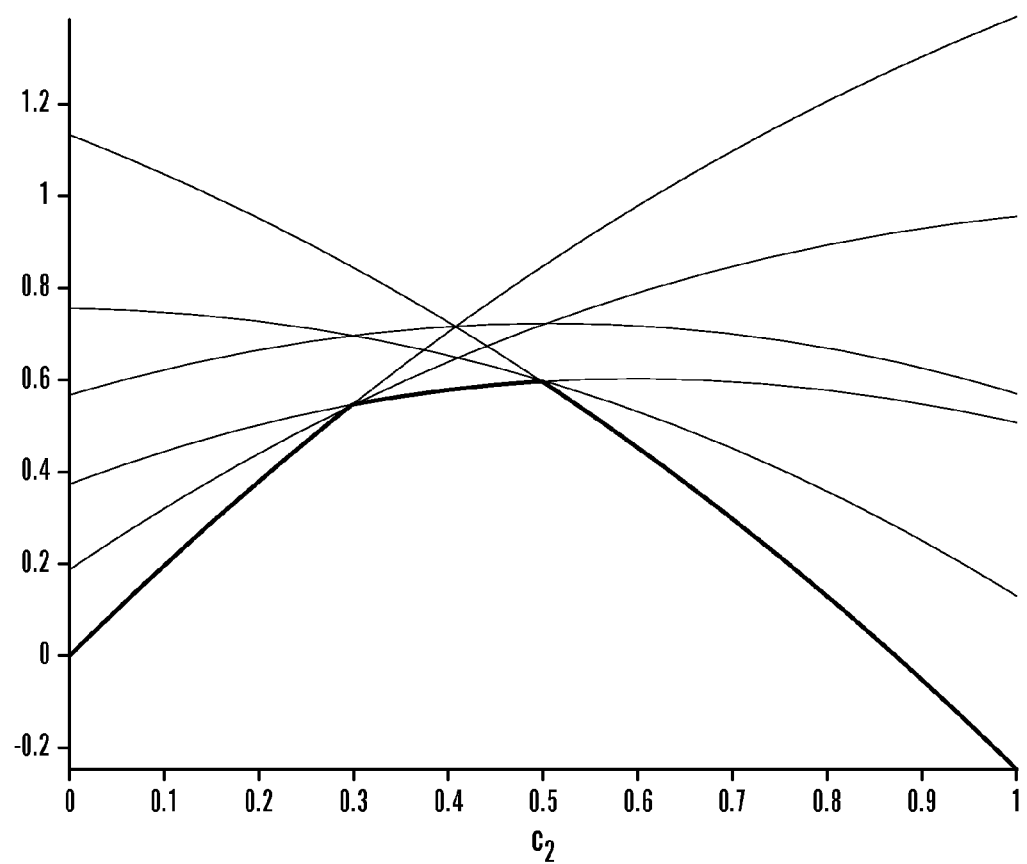
FIG. 8 illustrates parabolas.

The expression in (49) does not provide the maximum of (48); it is the maximum of one of nine possible parabolas corresponding to all the different combinations between the intervals of $g(\alpha_2, \epsilon_2)$ and $g(\gamma - s\alpha_2, \epsilon_1)$ in (42). Optimizing for $\alpha_1$ and $\alpha_2$ at any given step involves finding the maximum of (48), which is a piecewise concave function formed by the minimum of the set composed of the parabolas for a given $\alpha_2$, as can be seen in FIG. 8.

A method to optimize for the dual variables analytically way while avoiding evaluating the function $g(\alpha_i, \epsilon)$ is disclosed. As described above, optimizing a pair of dual variables involves finding the maximum of the piecewise concave function in (48). By taking advantage of the problem's structure, a procedure to obtain this maximum while avoiding any function evaluation and thus minimizing the necessary computations, is disclosed.

The steps of for finding the maximum of (48) are shown in FIG. 9. The goal is to evaluate (48) over the sequence of interval pairs of $\alpha_1$ and $\alpha_2$, clipping the maximum at the corresponding bound, until a maximum is reached. When the process starts the values of $$\frac{\partial}{\partial \alpha_2} g(\alpha_2, \varepsilon)$$

and $$\frac{\partial}{\partial \alpha_1} g(\alpha_1, \varepsilon)$$

are determined from the initial values of $\alpha_1$ and $\alpha_2$ (Step 1). These values can be 0, $-(1-\epsilon)$ and $-(1+\epsilon)$ for values of $\alpha_i$ in the intervals $0 \leq \alpha_i \leq Cw_c$, $Cw_c < \alpha_i \leq Cw_r$ and $Cw_r < \alpha_i \leq Cw_e$ respectively, as seen in (51). Then, the maximum of (48), $\alpha_2^{new}$, is obtained using (49) for $$\frac{\partial}{\partial \alpha_2} g(\alpha_2, \varepsilon)$$

and $$\frac{\partial}{\partial \alpha_1} g(\alpha_1, \varepsilon)$$

as determined in Step 1 and clipped in order to satisfy the linear constraint of Eq. 51 (Step 2 and Step 3). The corresponding value of $\alpha_1^{new}$ can then be calculated using $\alpha_1^{new} = \alpha_1 - s(\alpha_2 - \alpha_2^{new})$ (Step 4). Once $\alpha_2^{new}$ is computed, the ascent direction is obtained by $\text{sgn}(\alpha_2^{new} - \alpha_2)$ (Step 5). This will determine the upper bound on the interval, e.g. for the case where $Cw_c < \alpha_2^{new} \leq Cw_r$ the upper bound on $\alpha_2^{new}$ for a positive ascent direction will be $Cw_r$ while for a negative ascent direction the bound would be $Cw_c$. The next step (Step 6) is to verify that the values of $\alpha_2^{new}$ and $\alpha_1^{new}$ are within the respective interval used to determine their values. The computed $\alpha_2^{new}$ is the maximum of the parabola produced by the values of $$\frac{\partial}{\partial \alpha_2} g(\alpha_2, \varepsilon)$$

and $$\frac{\partial}{\partial \alpha_1} g(\alpha_1, \varepsilon)$$

for those particular intervals, and may or may not lie within them. In the case that these conditions are satisfied then $\alpha_2^{new}$ is the maximum (48) and the process stops. Otherwise, if either $\alpha_2^{new}$ and $\alpha_1^{new}$ are outside their respective interval, these values are clipped to the upper bound as determined by the ascent direction. If these last circumstances occur the value of $\alpha_2^{new}$ and/or $\alpha_1^{new}$ would correspond to a corner of (48). Then, verification of whether this corner is the maximum is performed; otherwise, the optimization process is continued (Step 7). To accomplish this, $\alpha_2^{next}$, the maximum of the parabola produced by the next interval, is computed, clipped so that $L \leq \alpha_2^{next} \leq H$ and the new ascent direction is obtained. If the new ascent direction changes then the maximum of (48) is at that corner and the process stops. Otherwise, the process continues with Step 6 until a maximum is found.

As described above, the SMO algorithm optimizes two Lagrange multipliers at each step. One of these multipliers has previously violated the KKT conditions before the step, i.e. SMO will always alter two Lagrange multipliers to move uphill in the objective function in (48) while maintaining a feasible Lagrange multiplier vector. Thus, at each step the overall objective function will increase until the algorithm converges asymptotically.

Two separate heuristics are used to choose the first and second multiplier. The choice of the first heuristic provides the outer loop of the algorithm. The outer loop first iterates over all samples in the training set, determining whether a sample violates the KKT conditions. Once a violated sample is found, a second multiplier is selected using the second choice heuristic and both are jointly optimized while maintaining feasibility. The SVM is updated using these two new values, and the outer loop resumes looking for KKT violators. To speed up training, the outer loop does not always cycle through the entire training set. After one pass through the training set, the outer loop iterates over non-bound samples only. These are defined as multipliers whose value are neither 0 nor C. The outer loop iterates over these samples until none of them violate the KKT conditions. Then the outer loop over the entire training set again. For the rest of the algorithm the outer loop alternates between these two until the entire set obeys the KKT conditions, and at this point the algorithm terminates.

The first choice heuristic is also used in the SMOER algorithm. In SMO, the outer loop concentrates most of the time in the non-bound samples, which are the ones most likely to violate KKT conditions. As the algorithm progresses, multipliers that are at the bounds are likely to stay there, while non-bound multipliers will change as others are optimized. In SMOER, the outer loop initially iterates over all samples, as in SMO, and then iterates over the non-corner samples. Non-corner samples are defined as multipliers whose values are neither 0, $Cw_c$, $Cw_r$, $Cw_e$, and are the samples most likely to change as the algorithm progresses. Like SMO, the outer loop alternates between iterating over all the samples and the non-corner samples until the KKT conditions are met for all samples, concentrating most of the time on the non-corner samples.

For selecting the second multiplier to optimize, SMOER uses the same heuristics as SMO. The objective in this step is to maximize the size of the step taken during joint optimization, which is approximated by the absolute value of the error difference in (49), $|E_1 - E_2|$. In the unusual circumstance that positive progress cannot be made using the heuristic described above, a hierarchy of second choice heuristics are used until positive progress is made when jointly optimizing a pair of multipliers. In that case, then SMOER iterates through the non-corner samples, starting at a random point, searching for a second multiplier that can make positive progress. If none of the non-corner samples accomplish this, the SMOER iterates through the entire training set, again starting at a random point, until a sample is found that makes positive progress. In the extreme case where none of the samples make positive progress when paired with the first multiplier, the first multiplier is skipped and SMOER continues with another chosen first multiplier.

A series of heuristics for selecting a pair of multipliers to optimize at a given iteration using KKT conditions were described above. The KKT conditions also play a role in the algorithm termination, as all samples must satisfy these conditions for SMO and SMOER to terminate.

The KKT condition is derived based on the values of the Lagrange multipliers. The following conditions are the result the optimality condition in (26), and the complementary slackness condition in (29) and (33) that result from the optimization problem in (22).

i. If $\alpha_i=0$, $\mu_i=Cw_c>0$, $\xi_i=0$;

$$y_i(w^t x_i - b) - 1 \geq 0.$$

ii. If $0<\alpha_i<Cw_c$, $\mu_i=Cw_c-\alpha_i>0$, $\xi_i=0$;

$$y_i(w^t x_i - b) - 1 = 0.$$

iii. If $\alpha_i=Cw_c$, $\mu_i=0$, $0<\xi_i<1-\epsilon$;

$$y_i(w^t x_i - b) - 1 = -\xi_i$$

$$-(1-\epsilon) < y_i(w^t x_i - b) - 1 < 0.$$

iv. If $Cw_c < \alpha_i < Cw_r$, $\mu_i=0$, $\xi_i=1-\epsilon$;

$$y_i(w^t x_i - b) - 1 = -(1-\epsilon).$$

v. If $\alpha_i=Cw_r$, $\mu_i=0$, $1-\epsilon < \xi_i < 1+\epsilon$;

$$y_i(w^t x_i - b) - 1 = -\xi_i$$

$$-(1+\epsilon) < y_i(w^t x_i - b) - 1 < -(1-\epsilon).$$

vi. If $Cw_r < \alpha_i < Cw_e$, $\mu_i=0$, $\xi_i=1+\epsilon$;

$$y_i(w^t x_i - b) - 1 = -(1+\epsilon).$$

vii. If $\alpha_i=Cw_e$, $\mu_i=0$, $\xi_i>1+\epsilon$;

$$y_i(w^t x_i - b) - 1 = -\xi_i$$

$$y_i(w^t x_i - b) - 1 < -(1+\epsilon).$$

As the SMOER algorithm iterates in the outer loop, the first choice heuristic selects a sample that has violated the KKT conditions as the first in the possible pair of multipliers that will be jointly optimized. The set of KKT violations checked in this step, and resulting from the previously outlined conditions, are summarized in FIG. 10.

Solving for the Lagrange multipliers does not determine the threshold b of the SVM and must be computed separately. In SMO, b is re-computed after each step, so that the KKT conditions are fulfilled for both optimized examples. The threshold is obtained by:

$$b_i = E_2 + y_1(a_1^{new} - a_1)k(x_1, x_i) + y_2(a_2^{new} - a_2)k(x_i, x_2) + b^{old}, \quad (52)$$

The threshold $b_i$ is valid when the new $\alpha_i$ is not at the bounds, i.e. $0<\alpha_i<C$, because it forces the output of the SVM to be $y_i$ when the input is $x_i$. When both new Lagrange multipliers are not at a bound, $b_1$ and $b_2$ are equal. In the case when both new multipliers are at a bound, then the interval between $b_1$ and $b_2$ are all thresholds that are consistent with the KKT conditions and SMO chooses the threshold to be halfway between $b_1$ and $b_2$.

The SMOER algorithm computes and updates the threshold b in a similar fashion. The only necessary modification in order to adapt how to compute the threshold in SMO to SMOER is by computing $b_i$, using (52), for multipliers whose value lie within 0 and $Cw_c$. In (37) it was seen that this range allowed for computing the threshold when solving the dual problem. Thus, in SMOER the threshold is updated only when values of the new Lagrange multipliers are within this range. As in SMO, when both new multipliers have values of 0 and/or $Cw_c$, the updated threshold is the value halfway between $b_1$ and $b_2$.

Using the convex formulation of SVM with embedded error-rejection solving a sub-problem with a sample that violates the KKT conditions improves the overall objective function and maintain feasibility. SMO and SMOER converge asymptotically by solving a series of these problems.

At any given iteration the value of b is updated based on the current pair of dual variables being optimized. In the case of SMOER this occurs is $\alpha_1$ and/or $\alpha_2$ lie between $0 \leq \alpha_i \leq Cw_c$, otherwise b is not updated. In SMO and SMOER, it is possible that a $\alpha_i$ values satisfy the KKT conditions might be mistakenly seen as violating them, and vice versa. This is the result of using sub-optimal values of b to check whether or not a $\alpha_i$ the KKT conditions. Thus it is possible to select a pair of dual variables to optimize that do not violate the KKT conditions and progress is not made. In this case, as a result of the choice heuristics, both SMO and SMOER continue looking for a pair of variables that do make progress.

Training the SVM with embedded-error rejection posed in (21) involves optimizing the primal variables w, b, $\xi_i$, $\epsilon$. Up to this point have been able to develop methods to optimize w, b, $\xi_i$ for a fixed value of $\epsilon$. The variable w is optimized when the solution to the dual variables, $\alpha_i$, is found with SMOER, while the threshold b is obtained during that process. The variable $\xi_i$ is analytically optimized when obtaining the expression in (42). The last piece in the development of a training algorithm for SVM with embedded error-rejection is optimizing $\epsilon$.

Recalling the problem stated in (40), using the expression in (42), and assuming that $\alpha_i$ is constant, $\epsilon$ are obtain by solving:

$$\min_{0 \leq \varepsilon \leq 1} \sum_i g(\alpha_i, \varepsilon). \quad (53)$$

To solve this problem, a subgradient method is used. This method utilizes the iteration $$\epsilon_{k+1} = \epsilon_k - \lambda_k d_k \quad (54)$$

where $\lambda_k$ is the step size at the $k^{th}$ iteration and $d_k$ is any subgradient of (53) at $\epsilon_k$. The sub differential of the objective function in (53) is $$\sum_i \frac{\partial g(\alpha_i, \varepsilon)}{\partial \varepsilon} \quad (55)$$

where $$\frac{\partial}{\partial \varepsilon} g(\alpha_i, \varepsilon) = \begin{cases} 0, & 0 \leq \alpha_i \leq Cw_c \\ -Cw_c + \alpha_i, & Cw_c < \alpha_i \leq Cw_r \\ C(2w_r - w_c) - \alpha_i, & Cw_r < \alpha_i \leq Cw_e. \end{cases} \quad (56)$$

The following step size rule is used ensuring convergence of the method:

$$\lambda_k = \frac{a|\varepsilon_k - \varepsilon_{k-1}|}{|d_k|}. \quad (57)$$

For values of $0<a<1$ this can be viewed as a diminishing step size rule. Furthermore, by selecting $\epsilon_{-1}=0$ if $d_0/|d_0|>0$ or $\epsilon_{-1}=1$ if $d_0/|d_0|<0$ in the initial step, the constraint $0 \leq \epsilon \leq 1$ is enforced.

The SVM with embedded error-rejection algorithm then consists of a series of iterations where the dual variables $\alpha_i$, and thus the primal variables w, b, $\xi_i$, are optimized followed by optimization of the primal variables $\epsilon$. The algorithm starts with some initial guess of ϵ, provided by the user. The developed SMOER routine is then called to optimize the dual variables with the initial values of ϵ. Next, the values of ϵ are updated using the subgradient method and the previously optimized values of $\alpha_i$. The algorithm keeps alternating between optimizing $\alpha_i$ and ϵ, until the convergence of ϵ.

The stopping criteria considered for convergence is $$|\epsilon_k - \epsilon_{k+1}| \le tol, \quad (58)$$

i.e. when the change in ϵ is less than a pre-determined tolerance.

There are cases where it might be of interest to assign training samples different costs, not only to misclassification but also to rejections, based on the class they belong to. This allows for handling applications where rejecting samples from one particular class is more costly that the other. For example, in colorectal cancer screening, it would be desirable to make a decision on non-dysplastic polyps based on ESS measurements while avoiding rejecting these as much as possible (and thus taking biopsies of them). Thus, a higher rejection cost could be assigned to these cases in the training process. This type of class-dependent weighting can be incorporated in the convex optimization problem for training support vector machines with embedded error-rejection by reformulating the problem as:

$$\min_{w,b,\xi_i,\varepsilon^+,\varepsilon^-} \frac{1}{2} w^T w + C^+ \sum_{i^+} h_c(\xi_i, \varepsilon^+) + C^- \sum_{i^-} h_c(\xi_i, \varepsilon^-) \quad (59)$$

$$\text{s.t.} \quad y_i(w^T x_i + b) \ge 1 - \xi_i$$
$$\xi_i \ge 0$$
$$0 \le \varepsilon^+, \varepsilon^- \le 1$$

where the superscripts +, − denote samples for which labels $y_i=1$ and $y_i=-1$ respectively. Thus, the solution of this problem constructs two separating hyperplanes of width $(\epsilon^+ + \epsilon^-)/\|w\|$ between them, that minimizes the sum of deviations, $\xi_i$, of training errors weighted by $w_c^+$, $w_r^+$, $w_e^+$ and $w_c^-$, $w_r^-$, $w_e^-$ accordingly. By obtaining the corresponding dual problem $$\max_{\alpha_i} \sum_i \alpha_i - \frac{1}{2} \sum_i \sum_j \alpha_i \alpha_j y_i y_j x_i^T x_j + \quad (60)$$

$$\min_{\substack{\xi_i,\varepsilon^+,\varepsilon^- \\ \xi_i \ge 0 \\ 0 \le \varepsilon^+,\varepsilon^- \le 1}} C^+ \sum_{i^+} h_c(\xi_i, \varepsilon^+) - \alpha_i \xi_i + C^- \sum_{i^-} h_c(\xi_i, \varepsilon^-) - \alpha_i \xi_i$$

$$\text{s.t.} \quad \sum_i \alpha_i y_i = 0$$
$$0 \le \alpha_i^{+,-} \le C^{+,-} w_e^{+,-}$$

Non-linear decision regions can also be obtained as well as the SMOER training algorithm described above can be used for training

EXAMPLES

Figure 11:
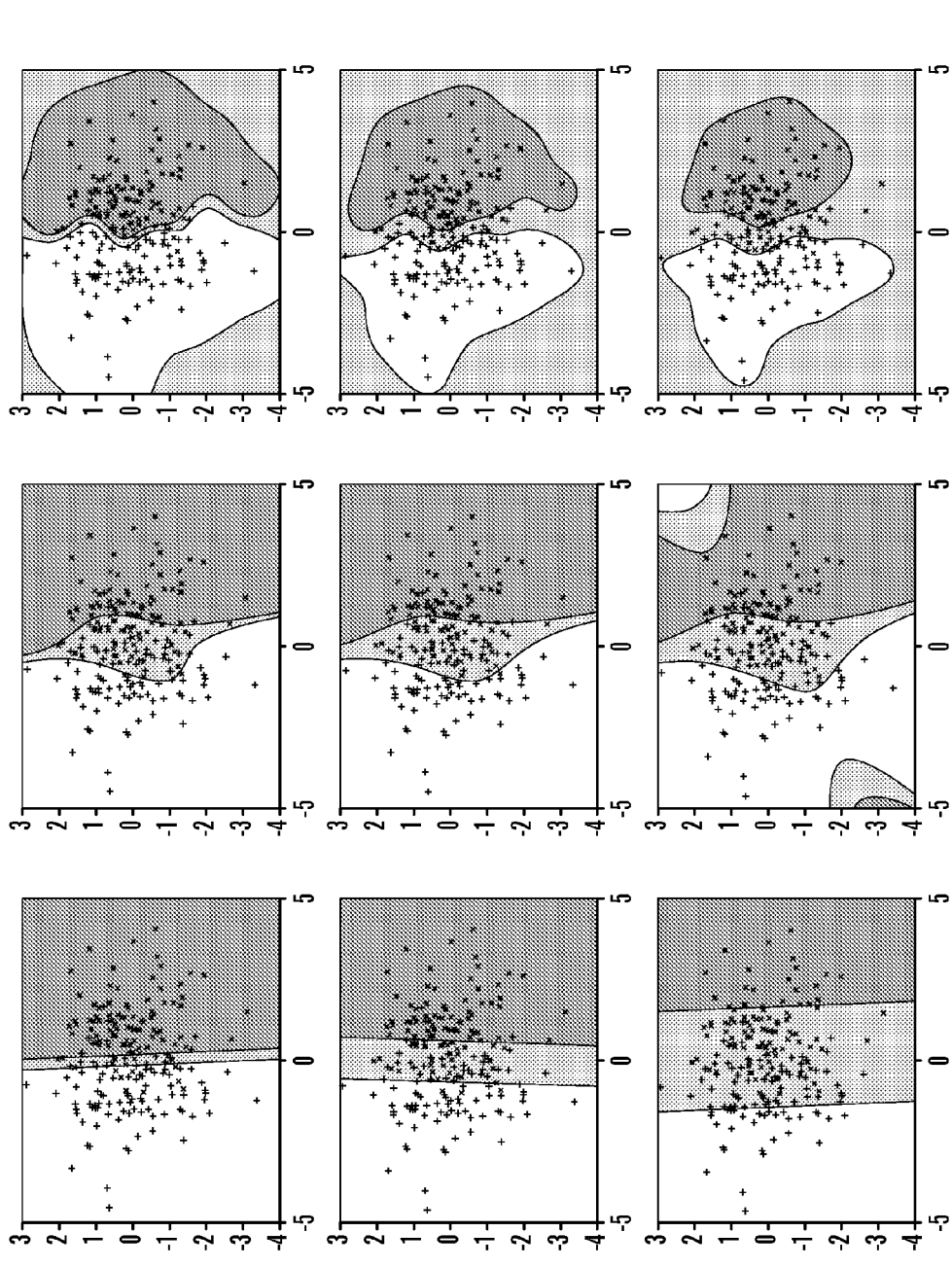
FIG. 11 illustrates rejection regions with different kernels.

The support vector machines with embedded error-rejection described above were tested. The first experiment applied the developed classifier to an artificial data consisting of two classes, and visually illustrated how the orientation and width of the rejection region varies for different rejection costs, $w_r$. Each class consists of 100 samples generated from a two-dimensional normal distribution with mean at [−1, 0] for one class and at [1,0] for the other. Both classes had a covariance equal to the identity matrix. Results are shown in FIG. 11 for the different kernels. In FIG. 11, results for a linear kernel are shown in the left column, a third degree polynomial in the center column and a RBF kernel in the right column. In FIG. 11, the rejection weight $w_r$ is decreased from the first row to the third row.

In the second experiment, the SVM with embedded error-rejection was used to classify the colon polyps dataset. The dimensionality of the data was reduced to 15 features using PCA. The SVMs were trained with embedded error-rejection with different values of the rejection cost $w_r$ and a sensitivity/specificity vs. rejection rate plot was generated. For comparison, results obtained by thresholding the outputs of a standard SVM with linear kernel were also generated in the form of the sensitivity/specificity vs. rejection rate plot. K-fold cross-validation was used, utilizing the same 50 random samplings of the data.

Figure 12:
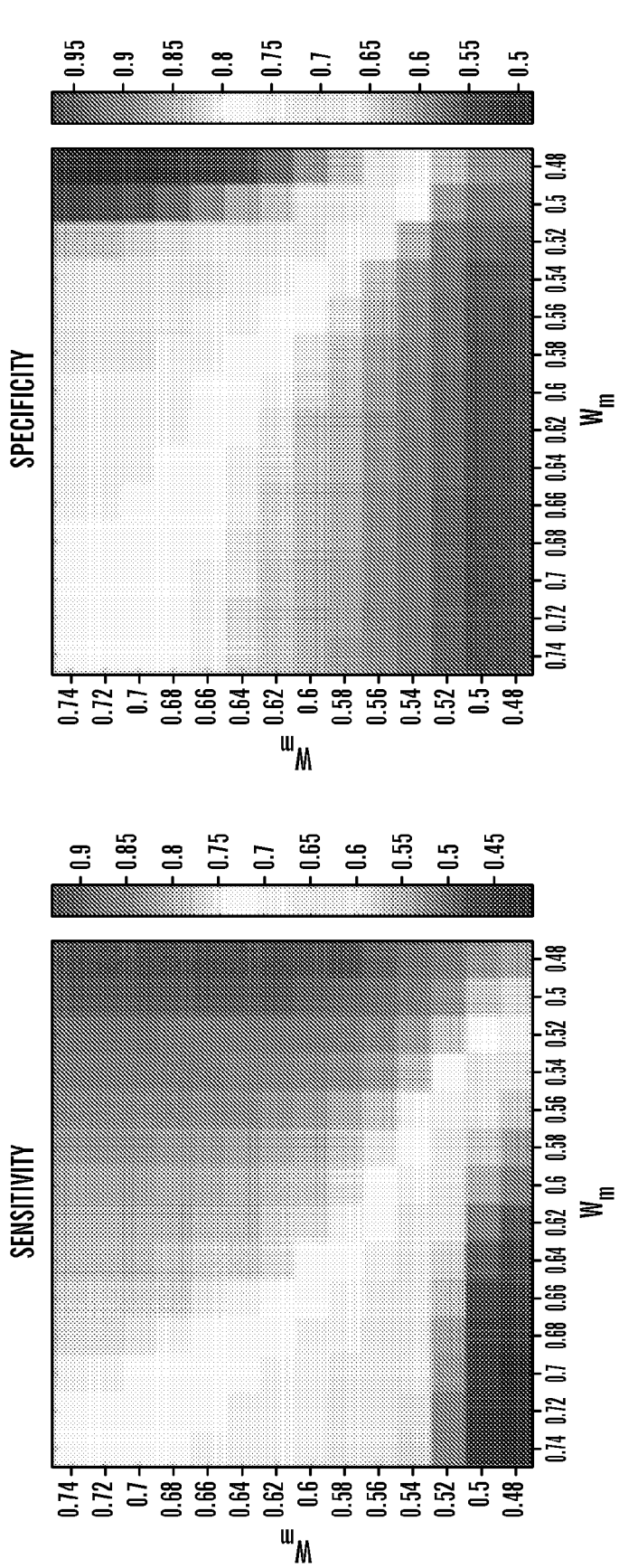
FIG. 12 illustrates class dependent weighting in a SVM classifier with SMOER and with a RBF kernel.
Figure 12:
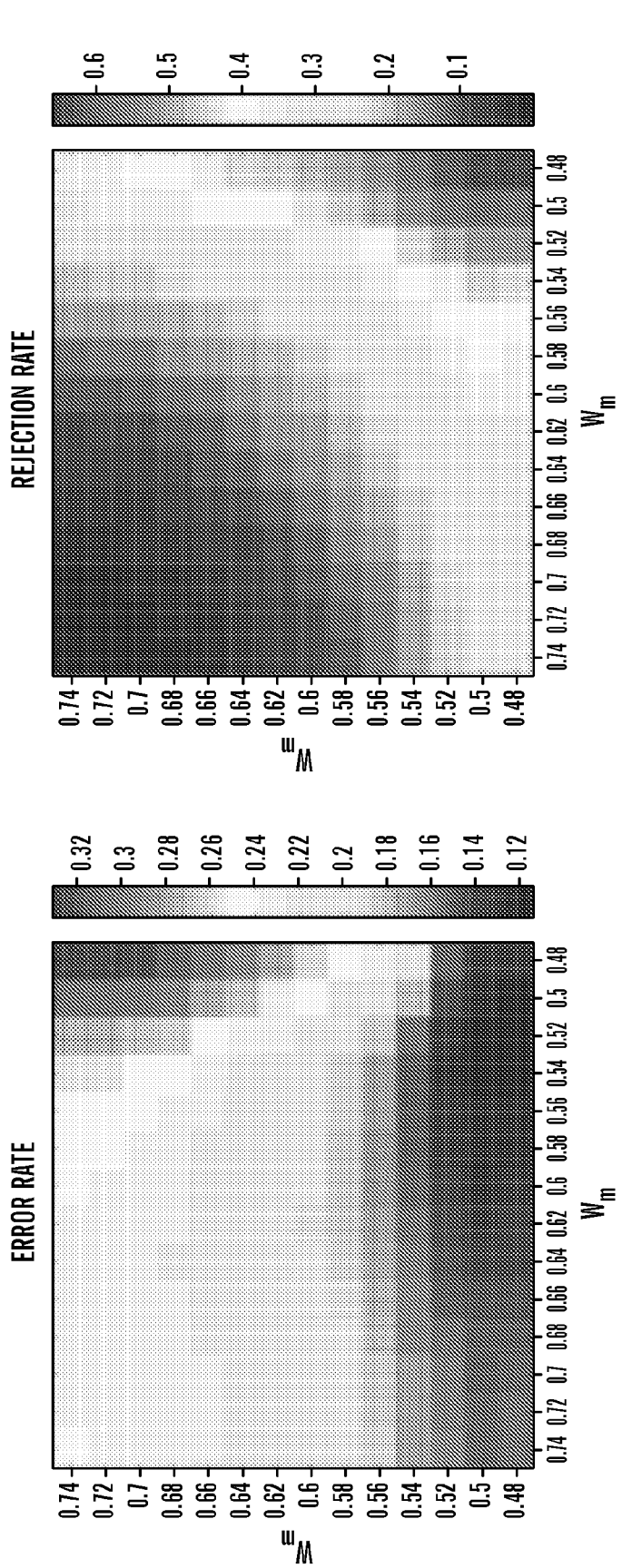
Figure 12:
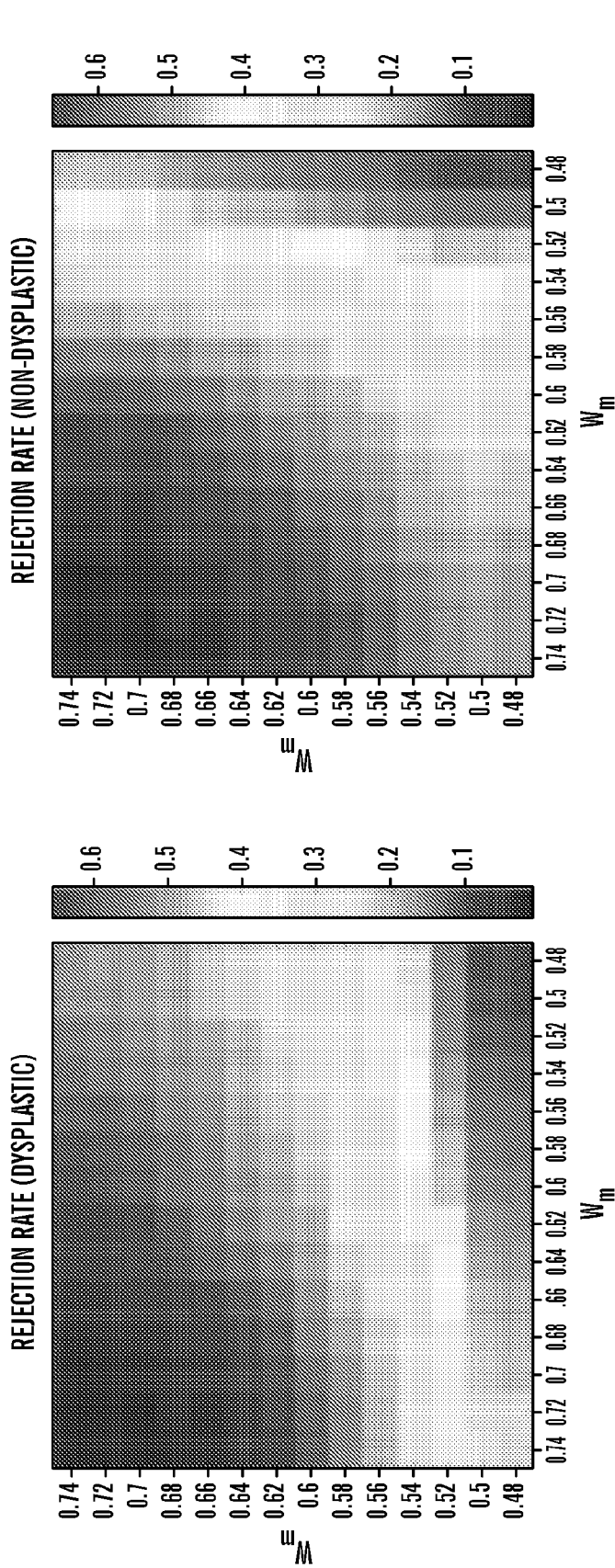

The final experiment illustrates the results obtained using class-dependents rejection weights $w_r^-$, $w_r^+$. For this example, again, the dimensionality of the data was reduced to 15 features using PCA. SVM with embedded error-rejection with RBF kernel was used. The rejection weights $w_r^-$, $w_r^+$ were varied independently to design classifiers with rejection regions of different orientations and widths. FIG. 12 illustrates the statistics obtained as the rejection weights were varied.

Results obtained by applying the developed convex formulation for SVM with embedded error-rejection show that obtaining the orientation and width of the decision region during the training process provides an improvement in performance over thresholding the outputs of a standard SVM. The results obtained using SVM with embedded error-rejection with linear kernel are comparable to or better than thresholding the outputs of a standard SVM with linear kernel. Additionally, further improvement can be obtained by using kernel functions to generate non-linear decision regions instead of just a linear kernel. While using the $2^{nd}$ and $3^{rd}$ degree polynomial kernels did not provide much improvement, the use of the RBF kernel had improved results. When using the RBF kernel higher sensitivity and, in particular, specificities are obtained for the same rejection rates when compared to values obtained by thresholding the outputs of a standard SVM. The use non-linear kernels allow for better identifying the region where misclassifications are more likely to occur, thus reducing the number of rejected samples that could be correctly classified. Finally, using class-dependent rejection weights permits designing classifiers that assign more cost to rejecting samples from one class. Since the rejection weights for each class are varied independently, the error-rejection or sensitivity/specificity-rejection curves now become two-dimensional surfaces. Classifiers can be designed for different sensitivities and specificities holding the overall rejection rate constant by varying the number of rejected samples from each class.

Multiple Classifier Systems

Figure 13:
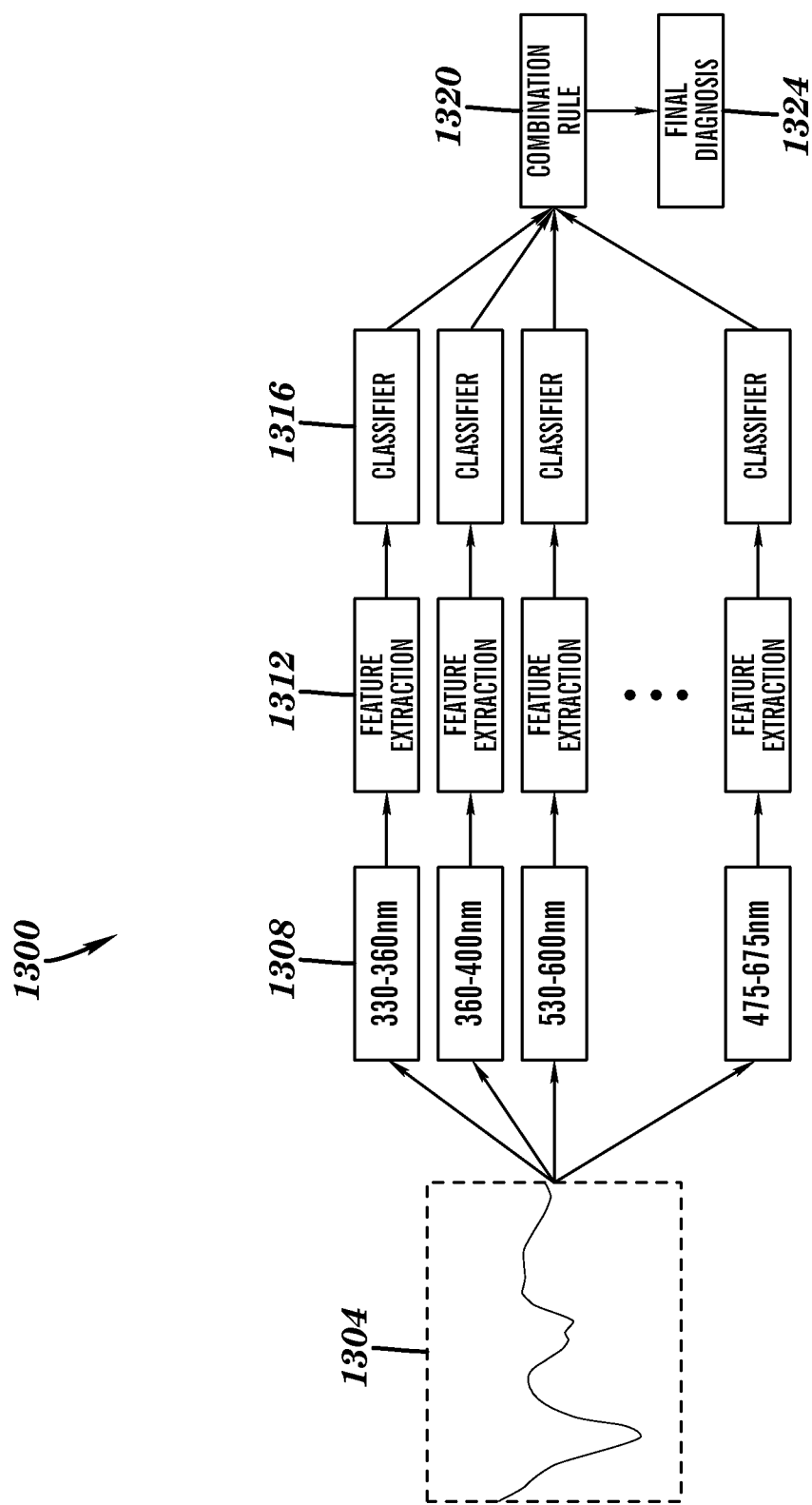
FIG. 13 illustrates a multiple classifier system.

Embodiments of the present invention are also directed to multiple classifier systems. These multiple classifier systems improve the overall sensitivity and specificity of the system. An exemplary multiple classifier system 1300 is shown in FIG. 13. As shown in FIG. 13, the multiple classifier system 1300 receives ESS spectrum data 1304 which includes different regions of spectra data 1308. A subset of the pattern features 1312 is identified as described above (e.g., feature selection using SFSS or SVDSS) for training. The system 1300 includes multiple classifiers 1316. The multiple classifiers 1316 are designed to operate in parallel. Each classifier 1316 is trained on a region of the ESS spectrum 1308. The final classification or diagnosis 1324 is obtained by combining the outputs of the base classifiers 1316 using a combination rule 1320.

The combination rule 1320 fuses the outputs of the classifiers 1316. Two exemplary combination rules that may be used are: majority voting and naive Bayes combiner. The majority voting rule assigns a sample the class label that 50%+1 of the base classifiers agree on. The naive Bayes combination rule is stated as follows: let x be a sample vector belonging to one of the possible $\omega_k$, k=1, K, c, classes. Also let L be the number of base classifiers in the ensemble. A sample x is said to belong to class $\omega_k$ if $\mu_k(x)$ is maximum, where $$\mu_k(x) \propto P(\omega_k) \prod_{i=1}^{L} P(y_i \mid \omega_k), \quad (61)$$

and $y_i$ are the output labels from the base classifiers. For the practical application of the binary classification problem, and assuming that if $y_i=1$ the sample is non-dysplastic and if $y_i=-1$ the sample is dysplastic, the conditional probabilities can be estimated as:

$P(y_i=-1 \mid \omega_k=-1)$=Sensitivity, $P(y_i=1 \mid \omega_k=-1)$=1−Sensitivity, $P(y_i=1 \mid \omega_k=1)$=Specificity, $P(y_i=-1 \mid \omega_k=1)$=1−Specificity.  (62)

$P(w_k)$ are the prior probabilities and can be estimated from the training data. Thus, this combination rule uses the performance of each base classifier, in the form of the sensitivity and specificity, to weight their decision.

In one embodiment, the classifiers 1316 are designed with error rejection as well. For example, the classifiers 1316 may be SVM classifiers with embedded error rejection as described above.

Example

Table 2 shows the classification results of a classifier designed using the whole spectrum, 330-760 nm, and a classifier using just the 330-400 nm region. The error rates for both classifiers was similar. Yet the errors were not necessarily committed on the same samples as illustrated by the difference in sensitivity and specificity.

TABLE 2

Classification results using the whole spectrum (330-760 nm) and using the 330-400 nm region. PCA and SVM with Linear Kernel were used.

| Region | # of Features | Sensitivity | Specificity | Error Rate |
|---|---|---|---|---|
| 330-760 nm | 15 | .7417 ± .0757 | .7538 ± .0528 | .2499 ± .0364 |
| 330-400 nm | 10 | .7977 ± .0732 | .7300 ± .0397 | .2490 ± .0276 |

Spectral regions were selected a priori in a heuristic fashion. Regions were chosen based on the areas of the spectrum that were shown to be more informative by using feature selection methods described above and based on where there was the most difference in the average spectrum for the dysplastic and non-dysplastic samples. Some regions were chosen to make sure that all areas of the spectrum were considered. The selected regions spanned across the whole spectrum and overlap between them was allowed. The main intent was to promote diversity by focusing on different areas of the ESS spectrum. In total, twenty-two regions were considered. Features on each region were obtained using PCA and the base classifier was a SVM. Two types of kernels were used: linear and RBF kernels. All results were obtained using K-fold cross-validation with the 50 randomly sampled sets described above.

Table 3 summarizes the performance of each individual classifier on each of the regions and shows the number of features extracted for each region. Although not shown, the standard deviation for the sensitivity, specificity and error rate were of around 0.08, 0.06 and 0.04 respectively.

TABLE 3

Performance of the SVM classifiers on each of the considered spectral regions.

| | | Liner Kernel | | | | RBF Kernel | | | |
|---|---|---|---|---|---|---|---|---|---|
| Index | Region | PC's | Se | Sp | Error Rate | PC's | Se | Sp | Error Rate |
| 1 | 330-760 nm | 15 | .7417 | .7538 | .2499 | 15 | .7463 | .7731 | .2365 |
| 2 | 330-800 nm | 15 | .7183 | .7546 | .2566 | 15 | .7206 | .7736 | .2428 |
| 3 | 330-600 nm | 12 | .7697 | .7392 | .2513 | 16 | .7629 | .7628 | .2372 |
| 4 | 330-380 nm | 5 | .7731 | .6626 | .3032 | 10 | .8000 | .6508 | .3030 |
| 5 | 330-360 nm | 8 | .7903 | .6469 | .3087 | 8 | .8000 | .6423 | .3088 |
| 6 | 330-400 nm | 10 | .7977 | .7300 | .2490 | 10 | .7914 | .7303 | .2508 |
| 7 | 360-400 nm | 6 | .7966 | .7156 | .2593 | 6 | .8046 | .7085 | .2618 |
| 8 | 530-600 nm | 7 | .6960 | .6913 | .3073 | 7 | .6966 | .6938 | .3053 |
| 9 | 460-590 nm | 14 | .6994 | .6826 | .3122 | 14 | .6966 | .6841 | .3120 |
| 10 | 360-600 nm | 12 | .7691 | .7305 | .2575 | 12 | .7737 | .7433 | .2535 |
| 11 | 360-760 nm | 14 | .6989 | .7621 | .2575 | 16 | .7206 | .7685 | .2464 |
| 12 | 360-800 nm | 13 | .6914 | .7721 | .2529 | 13 | .6920 | .7726 | .2524 |
| 13 | 500-600 nm | 9 | .6794 | .7003 | .3062 | 9 | .6863 | .7105 | .2970 |
| 14 | 590-760 nm | 12 | .6160 | .7131 | .3170 | 11 | .6166 | .7174 | .3138 |
| 15 | 590-700 nm | 9 | .6211 | .7462 | .2926 | 9 | .6240 | .7487 | .2899 |

TABLE 3-continued

Performance of the SVM classifiers on each of the considered spectral regions.

| | | Liner Kernel | | | | RBF Kernel | | | |
|---|---|---|---|---|---|---|---|---|---|
| Index | Region | PC's | Se | Sp | Error Rate | PC's | Se | Sp | Error Rate |
| 16 | 590-800 nm | 15 | .6463 | .7072 | .3117 | 14 | .6423 | .7172 | .3060 |
| 17 | 700-760 nm | 6 | .5046 | .6385 | .4030 | 6 | .4817 | .6636 | .3927 |
| 18 | 700-800 nm | 7 | .5903 | .6690 | .3554 | 7 | .5909 | .6708 | .3540 |
| 19 | 460-700 nm | 14 | .6577 | .7110 | .3055 | 17 | .6594 | .7274 | .2936 |
| 20 | 500-760 nm | 7 | .6274 | .6946 | .3262 | 15 | .6377 | .7162 | .3081 |
| 21 | 500-700 nm | 16 | .6794 | .7438 | .2761 | 16 | .6829 | .7449 | .2743 |
| 22 | 400-760 nm | 11 | .6954 | .7321 | .2793 | 12 | .7000 | .7323 | .2777 |

First, all combinations of size 3, 5, 7, 9 were selected from the twenty-two possible classifiers. For each combination, the majority voting combination rule was used to obtain the final decision. For each size (3, 5, 7, 9), the combination of regions that resulted in the best average recognition rate (ARR, average between sensitivity and specificity), error rate, sensitivity and specificity was selected. The results are shown in Table 4. This was repeated with the naive Bayes combiner, yielding the results in Table 5.

TABLE 4

Summary of results with Majority Voting combination rule.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 3, 7, 21 | 3, 7, 15 | 3, 5, 6 | 1, 7, 15 | 3, 7, 21 | 1, 7, 21 | 1, 5, 6 | 2, 11, 18 |
| | Sen | .7966 | .7806 | .8234 | .7623 | .7994 | .7794 | .8251 | .7091 |
| | Spe | .7751 | .7846 | .7115 | .7897 | .7721 | .7846 | .7233 | .7944 |
| | Error | .2182 | .2166 | .2538 | .2188 | .2195 | .2170 | .2451 | .2320 |
| 5 | Reg | 1, 3, 7, 15, 21 | 1, 3, 7, 15, 21 | 3, 4, 5, 6, 7 | 3, 7, 12, 15, 21 | 1, 3, 5, 6, 21 | 1, 3, 7, 18, 21 | 1, 4, 5, 6, 10 | 1, 2, 7, 15, 18 |
| | Sen | .7760 | .7760 | .8183 | .7480 | .8091 | .7606 | .8251 | .7417 |
| | Spe | .7921 | .7921 | .7044 | .7967 | .7644 | .7990 | .7069 | .8021 |
| | Error | .2129 | .2129 | .2604 | .2184 | .2218 | .2129 | .2565 | .2166 |
| 7 | Reg | 1, 3, 6, 7, 15, 19, 21 | 1, 3, 6, 7, 15, 19, 21 | 3, 4, 5, 6, 7, 8, 10 | 3, 7, 11, 12, 15, 18, 21 | 1, 3, 7, 10, 13, 15, 21 | 1, 2, 7, 11, 15, 18, 21 | 1, 3, 4, 5, 6, 7, 9 | 1, 2, 7, 11, 15, 17, 18 |
| | Sen | .7806 | .7806 | .8171 | .7349 | .7869 | .7480 | .8223 | .7200 |
| | Spe | .7879 | .7879 | .7146 | .7954 | .7790 | .8031 | .7215 | .8044 |
| | Error | .2143 | .2143 | .2536 | .2234 | .2186 | .2140 | .2473 | .2218 |
| 9 | Reg | 3, 4, 5, 6, 7, 10, 15, 21, 22 | 1, 3, 6, 7, 10, 15, 18, 19, 21 | 3, 4, 5, 6, 7, 8, 10, 11, 21 | 1, 2, 3, 7, 12, 15, 17, 18, 21 | 1, 3, 5, 6, 10, 16, 19, 21, 22 | 1, 2, 6, 7, 11, 13, 15, 18, 21 | 1, 3, 4, 5, 6, 7, 8, 9, 10 | 1, 2, 3, 7, 11, 15, 17, 18, 21 |
| | Sen | .8046 | .7703 | .8114 | .7217 | .7851 | .7606 | .8103 | .7314 |
| | Spe | .7551 | .7885 | .7413 | .7954 | .7777 | .7959 | .7297 | .8028 |
| | Error | .2296 | .2172 | .2370 | .2274 | .2200 | .2150 | .2453 | .2193 |

TABLE 5

Summary of results with Naive Bayes combination rule.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 3, 7, 21 | 1, 7, 17 | 6, 7, 15 | 3, 17, 21 | 1, 7, 21 | 1, 7, 17 | 6, 7, 13 | 13, 17, 18 |
| | Sen | .7480 | .6720 | .7686 | .5920 | .7417 | .6823 | .7737 | .4903 |
| | Spe | .8200 | .8662 | .7697 | .8767 | .8279 | .8597 | .7682 | .8813 |

TABLE 5-continued

Summary of results with Naive Bayes combination rule.

| | | Linear Kernel | | | | RBF Kernel | | | |
|---|---|---|---|---|---|---|---|---|---|
| L | | ARR | Error | Sen | Spe | ARR | Error | Sen | Spe |
| | Error | .2023 | .1940 | .2306 | .2115 | .1988 | .1952 | .2301 | .2398 |
| 5 | Reg | 3, 5, 7, 21, 22 | 3, 7, 12, 17, 21 | 3, 5, 6, 7, 13 | 1, 7, 17, 18, 21 | 1, 7, 10, 17, 21 | 1, 7, 10, 17, 21 | 1, 3, 5, 6, 10 | 1, 7, 17, 18, 19 |
| | Sen | .7577 | .7166 | .7771 | .6869 | .7526 | .7526 | .7783 | .6863 |
| | Spe | .8136 | .8397 | .7759 | .8495 | .8262 | .8262 | .7944 | .8487 |
| | Error | .2037 | .1984 | .2237 | .2009 | .1966 | .1966 | .2106 | .2016 |
| 7 | Reg | 3, 4, 6, 7, 8, 21, 22 | 3, 6, 7, 12, 17, 18, 21 | 3, 5, 6, 7, 8, 10, 21 | 3, 7, 9, 15, 17, 18, 21 | 1, 3, 5, 6, 7, 21, 22 | 1, 3, 7, 17, 18, 19, 21 | 1, 2, 4, 5, 6, 7, 17 | 2, 3, 7, 15, 17, 18, 21 |
| | Sen | .7800 | .7371 | .7823 | .6960 | .7766 | .7331 | .7834 | .7240 |
| | Spe | .7936 | .8290 | .7859 | .8323 | .8013 | .8315 | .7674 | .8341 |
| | Error | .2106 | .1995 | .2152 | .2099 | .2064 | .1989 | .2276 | .2000 |
| 9 | Reg | 1, 3, 5, 6, 7, 10, 15, 19, 21 | 3, 6, 7, 12, 13, 15, 17, 18, 21 | 3, 4, 5, 6, 7, 8, 10, 20, 22 | 3, 6, 7, 12, 15, 16, 17, 18, 21 | 1, 2, 3, 5, 6, 7, 15, 17, 21 | 1, 2, 3, 7, 13, 15, 17, 18, 21 | 1, 3, 4, 5, 6, 7, 10, 17, 21 | 3, 6, 7, 12, 15, 16, 17, 18, 21 |
| | Sen | .7737 | .7411 | .7834 | .7320 | .7709 | .7526 | .7846 | .7320 |
| | Spe | .7951 | .8215 | .7718 | .8228 | .8059 | .8215 | .7818 | .8264 |
| | Error | .2115 | .2034 | .2246 | .2053 | .2050 | .1998 | .2173 | .2028 |

As seen in Table 3, the performance of the classifiers designed on each of the considered regions were varied, with some like 3 (330-600 nm), 6 (330-400 nm), 7 (360-400 nm) and 10 (360-600 nm) yielding particularly good results. This varied effectiveness encourages their use in ensemble classifiers. From the results, combinations of different regions provide an increase in classification performance when compared to just a single classifier. Both combination rules evaluated managed to yield better results, with the naive Bayes combiner seemingly working the best.

ESS Optical Biopsy Diagnostic Method

Embodiments of the present invention are also directed to a method for making decisions or diagnoses based on the ESS measurements. The method begins with a dimensionality reduction step to handle the high dimensional measurements generated by ESS. This step focuses on different, and often smaller, areas of the ESS spectrum. The method continues by training each of the multiple classifiers on one of the smaller areas of the ESS spectrum. In one embodiment, the multiple classifiers are trained with embedded error rejection. The method continues, during a diagnosis phase, by classifying spectra data for a tissue sample by each of the multiple classifiers. Each classifier analyzes the spectra data for the sample on which that classifier was trained. In embodiments in which the multiple classifiers are trained with embedded error rejection, the decision of the classifier can be positive, reject or negative $\{+1, 0, -1\}$; otherwise, the decision will be positive or negative $\{+1, 0, -1\}$. The method then continues by combining the classification of each of the classifiers to determine a final diagnosis of the tissue sample.

With the inclusion of the reject option in three base classifiers, because the output of these classifiers is $\{-1, 0, 1\}$, a modification to the combination rules is required. Combining the decisions of the base classifiers is now a two-step process: first, it is decided whether the sample is rejected; second, if the sample is not rejected, a decision is made based on the classifiers that assigned a label, i.e. didn't reject the sample. A majority rule can be used to determine whether to reject a sample. A sample is rejected if 50%+1 of the base classifiers withheld from assigning a label. For samples that are not rejected, any given combination rule can be applied to those classifiers that did not withhold from making a decision. Again, the majority voting and naive Bayes combination rules can be used.

Example

All of the ESS spectral regions used above were again used in this example. PCA was used to reduce dimensionality and the number of features used is the same as in the previous section (summarized in Table 3). SVMs with embedded error-rejection, with linear and RBF kernels, were trained on each region for different rejection rates by varying the rejection cost. To build the multiple classifier system, classifiers at a particular rejection rate were selected from each of the regions (specifically, rejection rates of around 0.33 and 0.50 were used) for the base classifiers. In Tables 6 and 7 the performance for the classifiers in each region, for 0.33 and 0.50 rejection rate respectively, are summarized.

K-fold cross-validation with 50 randomly sampled sets was used. The combination of regions that yielded the best average recognition rate (ARR, average between sensitivity and specificity), error rate, sensitivity and specificity from all possible ensembles of size L=$\{3, 5, 7, 9\}$ that can be created were used. The standard deviation for the sensitivities, specificities, error rates and rejection rates hovered around 0.08, 0.06, 0.04 and 0.05 respectively. The results are summarized in Tables 8 and 9 for a base classifier rejection rate of about 0.33 using majority voting and naive Bayes combiner respectively. For base classifiers with rejection rate of about 0.50 the results are summarized in Table 10, for majority voting, and Table 11, for naive Bayes combiner.

TABLE 6

Performance of the classifiers with .33 rejection rate on each of the considered spectral regions.

| | | Liner Kernel | | | | RBF Kernel | | | |
|---|---|---|---|---|---|---|---|---|---|
| Index | Region | Sen | Spe | Error | Rej | Sen | Spe | Error | Rej |
| 1 | 330-760 nm | .7891 | .8282 | .1823 | .3046 | .7990 | .8526 | .1624 | .3248 |
| 2 | 330-800 nm | .7668 | .8287 | .1883 | .3120 | .7830 | .8542 | .1668 | .3407 |
| 3 | 330-600 nm | .8277 | .8222 | .1747 | .3193 | .8317 | .8401 | .1618 | .3207 |
| 4 | 330-380 nm | .8142 | .7151 | .2561 | .2927 | .8004 | .7472 | .2379 | .3301 |
| 5 | 330-360 nm | .8292 | .7265 | .2442 | .3531 | .8142 | .7333 | .2438 | .3335 |
| 6 | 330-400 nm | .8605 | .7923 | .1879 | .2915 | .8633 | .8007 | .1806 | .3370 |
| 7 | 360-400 nm | .8633 | .7735 | .1990 | .3312 | .8587 | .7773 | .1976 | .3177 |
| 8 | 530-600 nm | .7487 | .7464 | .2518 | .3465 | .7400 | .7479 | .2541 | .3322 |
| 9 | 460-590 nm | .7381 | .7435 | .2582 | .2975 | .7388 | .7534 | .2508 | .3248 |
| 10 | 360-600 nm | .8389 | .8325 | .1648 | .3634 | .8322 | .8298 | .1693 | .3262 |
| 11 | 360-760 nm | .7712 | .8148 | .1977 | .3358 | .7971 | .8365 | .1752 | .3372 |
| 12 | 360-800 nm | .7585 | .8234 | .1957 | .3519 | .7530 | .8206 | .1993 | .3287 |
| 13 | 500-600 nm | .7427 | .7519 | .2500 | .3283 | .7380 | .7566 | .2482 | .3352 |
| 14 | 590-760 nm | .6619 | .7653 | .2682 | .3039 | .6733 | .7674 | .2632 | .3400 |
| 15 | 590-700 nm | .6983 | .7937 | .2364 | .3205 | .7061 | .7974 | .2313 | .3416 |
| 16 | 590-800 nm | .7042 | .7838 | .2407 | .3605 | .7093 | .7762 | .2445 | .3281 |
| 17 | 700-760 nm | .5530 | .6470 | .3828 | .2888 | .5709 | .6389 | .3810 | .3299 |
| 18 | 700-800 nm | .6162 | .6955 | .3294 | .3676 | .6257 | .6779 | .3392 | .3184 |
| 19 | 460-700 nm | .7135 | .7580 | .2559 | .3122 | .7035 | .7882 | .2386 | .3150 |
| 20 | 500-760 nm | .6967 | .7535 | .2637 | .3412 | .7105 | .7676 | .2497 | .3411 |
| 21 | 500-700 nm | .7176 | .8153 | .2156 | .3644 | .7156 | .8107 | .2196 | .3432 |
| 22 | 400-760 nm | .7777 | 7983 | .2067 | .3681 | .7663 | .7935 | .2138 | .3384 |

TABLE 7

Performance of the classifiers with .50 rejection rate on each of the considered spectral regions.

| | | Liner Kernel | | | | RBF Kernel | | | |
|---|---|---|---|---|---|---|---|---|---|
| Index | Region | Sen | Spe | Error | Rej | Sen | Spe | Error | Rej |
| 1 | 330-760 nm | .8157 | .8440 | .1618 | .4772 | .8150 | .8862 | .1334 | .5131 |
| 2 | 330-800 nm | .7996 | .8575 | .1571 | .5000 | .8052 | .8822 | .1394 | .5306 |
| 3 | 330-600 nm | .8261 | .8498 | .1541 | .5002 | .8449 | .8666 | .1381 | .4940 |
| 4 | 330-380 nm | .8296 | .7380 | .2337 | .4584 | .8129 | .7699 | .2167 | .5019 |
| 5 | 330-360 nm | .8600 | .7455 | .2210 | .5370 | .8473 | .7580 | .2157 | .5041 |
| 6 | 330-400 nm | .8726 | .8279 | .1575 | .4846 | .8750 | .8258 | .1584 | .4885 |
| 7 | 360-400 nm | .8803 | .8111 | .1675 | .5159 | .8899 | .7890 | .1790 | .4919 |
| 8 | 530-600 nm | .7646 | .7736 | .2288 | .5310 | .7626 | .7643 | .2353 | .4894 |
| 9 | 460-590 nm | .7609 | .7721 | .2305 | .4669 | .7692 | .7805 | .2227 | .4837 |
| 10 | 360-600 nm | .8697 | .8533 | .1401 | .4558 | .8812 | .8665 | .1265 | .5260 |
| 11 | 360-760 nm | .8080 | .8477 | .1632 | .5333 | .8248 | .8625 | .1472 | .4749 |
| 12 | 360-800 nm | .7993 | .8450 | .1667 | .5533 | .7846 | .8470 | .1701 | .5193 |
| 13 | 500-600 nm | .7587 | .7926 | .2184 | .5030 | .7624 | .7863 | .2209 | .4927 |
| 14 | 590-760 nm | .7006 | .7883 | .2392 | .4828 | .7054 | .8052 | .2255 | .5023 |
| 15 | 590-700 nm | .7372 | .8266 | .2019 | .4634 | .7587 | .8437 | .1830 | .5152 |
| 16 | 590-800 nm | .7142 | .7976 | .2274 | .4533 | .7391 | .8128 | .2089 | .5145 |
| 17 | 700-760 nm | .5326 | .7092 | .3485 | .4805 | .5494 | .7073 | .3435 | .5023 |
| 18 | 700-800 nm | .6130 | .7167 | .3173 | .4646 | .6313 | .7044 | .3191 | .4901 |
| 19 | 460-700 nm | .7445 | .7833 | .2268 | .4779 | .7537 | .8356 | .1895 | .5129 |
| 20 | 500-760 nm | .7287 | .8002 | .2218 | .5204 | .7415 | .8042 | .2151 | .5067 |
| 21 | 500-700 nm | .7488 | .8531 | .1791 | .5453 | .7415 | .8447 | .1884 | .5150 |
| 22 | 400-760 nm | .7906 | .8150 | .1910 | .4487 | .7943 | .8280 | .1809 | .5104 |

TABLE 8

Summary of results with Majority Voting combination rule and base classifiers with .33 rejection rate.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 3, 7, 10 | 6, 10, 21 | 6, 7, 10 | 1, 10, 12 | 3, 7, 10 | 3, 6, 21 | 6, 7, 10 | 1, 2, 11 |
| | Sen | .8738 | .8486 | .8831 | .8027 | .8629 | .8400 | .8832 | .7995 |
| | Spe | .8345 | .8459 | .8007 | .8527 | .8360 | .8507 | .8052 | .8593 |
| | Error | .1528 | .1526 | .1750 | .1615 | .1560 | .1520 | .1716 | .1576 |
| | Rej | .3308 | .2995 | .3156 | .3315 | .3152 | .2945 | .3177 | .3338 |
| 5 | Reg | 3, 5, 7, 10, 21 | 3, 7, 10, 16, 21 | 3, 5, 6, 7, 10 | 3, 7, 10, 16, 21 | 3, 6, 7, 10, 19 | 2, 3, 7, 19, 21 | 3, 6, 7, 10, 19 | 2, 6, 11, 19, 21 |
| | Sen | .8520 | .8301 | .8645 | .8301 | .8722 | .8268 | .8722 | .8004 |
| | Spe | .8392 | .8582 | .8085 | .8582 | .8250 | .8585 | .8250 | .8615 |
| | Error | .1559 | .1505 | .1747 | .1505 | .1609 | .1511 | .1609 | .1571 |
| | Rej | .3081 | .3041 | .2954 | .3041 | .2894 | .2828 | .2894 | .2952 |
| 7 | Reg | 3, 5, 6, 7, 10, 16, 21 | 1, 3, 5, 7, 10, 16, 21 | 3, 4, 5, 6, 7, 10, 18 | 3, 5, 7, 10, 16, 20, 21 | 1, 2, 3, 6, 7, 10, 22 | 1, 2, 3, 6, 7, 10, 22 | 1, 3, 5, 6, 7, 10, 19 | 1, 2, 6, 11, 16, 19, 21 |
| | Sen | .8555 | .8356 | .8609 | .8101 | .8414 | .8414 | .8580 | .8015 |
| | Spe | .8387 | .8493 | .7960 | .8565 | .8523 | .8523 | .8327 | .8600 |
| | Error | .1562 | .1546 | .1845 | .1575 | .1503 | .1503 | .1595 | .1576 |
| | Rej | .2869 | .2963 | .2685 | .3002 | .3019 | .3019 | .2802 | .2890 |
| 9 | Reg | 1, 3, 5, 6, 7, 10, 13, 16, 21 | 1, 3, 5, 6, 7, 10, 13, 16, 21 | 1, 3, 4, 5, 6, 7, 10, 13, 16 | 2, 3, 5, 7, 8, 10, 16, 18, 21 | 1, 3, 5, 6, 7, 10, 13, 16, 19 | 1, 3, 5, 6, 7, 10, 13, 16, 19 | 3, 4, 5, 6, 7, 8, 10, 11, 16 | 3, 4, 7, 11, 13, 15, 16, 17, 21 |
| | Sen | .8440 | .8440 | .8512 | .8172 | .8467 | .8467 | .8530 | .7852 |
| | Spe | .8437 | .8437 | .8207 | .8526 | .8466 | .8466 | .8307 | .8556 |
| | Error | .1557 | .1557 | .1698 | .1580 | .1534 | .1534 | .1633 | .1661 |
| | Rej | .2841 | .2841 | .2738 | .2841 | .2687 | .2687 | .2775 | .2628 |

TABLE 9

Summary of results with Naive Bayes combination rule and base classifiers with .33 rejection rate.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 3, 7, 10 | 3, 7, 22 | 6, 7, 10 | 2, 7, 21 | 3, 7, 10 | 3, 7, 16 | 6, 7, 10 | 1, 7, 21 |
| | Sen | .8644 | .8308 | .8710 | .7724 | .8569 | .8267 | .8706 | .7903 |
| | Spe | .8576 | .8768 | .8204 | .8872 | .8514 | .8797 | .8221 | .8862 |
| | Error | .1399 | .1372 | .1646 | .1483 | .1470 | .1368 | .1637 | .1433 |
| | Rej | .3308 | .3181 | .3165 | .2959 | .3152 | .2823 | .3177 | .2938 |
| 5 | Reg | 3, 6, 7, 10, 22 | 3, 7, 10, 16, 21 | 3, 6, 7, 10, 22 | 3, 7, 16, 18, 21 | 1, 3, 6, 7, 22 | 2, 3, 7, 19, 21 | 3, 6, 7, 10, 19 | 3, 7, 16, 17, 21 |
| | Sen | .8607 | .8249 | .8607 | .7659 | .8512 | .8158 | .8668 | .7769 |
| | Spe | .8402 | .8673 | .8402 | .8753 | .8535 | .8723 | .8358 | .8755 |
| | Error | .1536 | .1462 | .1536 | .1597 | .1466 | .1452 | .1550 | .1554 |
| | Rej | .3048 | .3041 | .3048 | .2949 | .2945 | .2828 | .2899 | .2550 |
| 7 | Reg | 3, 5, 6, 7, 10, 16, 21 | 3, 6, 7, 10, 16, 18, 21 | 3, 5, 6, 7, 8, 10, 22 | 3, 6, 7, 10, 16, 18, 21 | 1, 2, 3, 6, 7, 10, 22 | 1, 2, 3, 6, 7, 10, 22 | 3, 5, 6, 7, 10, 13, 19 | 2, 3, 7, 13, 16, 18, 21 |
| | Sen | .8477 | .8260 | .8529 | .8260 | .8417 | .8417 | .8510 | .7900 |
| | Spe | .8556 | .8674 | .8394 | .8674 | .8590 | .8590 | .8398 | .8700 |
| | Error | .1472 | .1455 | .1563 | .1455 | .1458 | .1458 | .1569 | .1548 |
| | Rej | .2869 | .2789 | .2972 | .2789 | .3019 | .3019 | .2759 | .2627 |
| 9 | Reg | 1, 3, 5, 6, 7, 8, 10, 16, 21 | 3, 5, 6, 7, 10, 16, 18, 21, 22 | 1, 3, 4, 5, 6, 7, 10, 13, 16 | 2, 3, 6, 7, 10, 15, 16, 18, 21 | 1, 3, 5, 6, 7, 10, 13, 16, 22 | 1, 2, 3, 6, 7, 11, 13, 16, 22 | 1, 3, 4, 5, 6, 7, 8, 10, 16 | 2, 3, 5, 7, 13, 15, 16, 17, 21 |
| | Sen | .8393 | .8284 | .8483 | .8140 | .8455 | .8316 | .8482 | .7896 |
| | Spe | .8554 | .8616 | .8328 | .8650 | .8532 | .8613 | .8382 | .8679 |
| | Error | .1494 | .1487 | .1626 | .1508 | .1493 | .1475 | .1588 | .1565 |
| | Rej | .2848 | .2743 | .2738 | .2712 | .2729 | .2862 | .2761 | .2572 |

TABLE 10

Summary of results with Majority Voting combination rule and base classifiers with .50 rejection rate.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 3, 7, 10 | 6, 10, 21 | 6, 7, 10 | 3, 10, 21 | 1, 7, 10 | 1, 10, 16 | 6, 7, 10 | 1, 10, 21 |
| | Sen | .8892 | .8702 | .9001 | .8564 | .8983 | .8651 | .9043 | .8612 |
| | Spe | .8661 | .8807 | .8440 | .8830 | .8764 | .8984 | .8442 | .8988 |
| | Error | .1256 | .1216 | .1391 | .1234 | .1154 | .1106 | .1368 | .1115 |
| | Rej | .4949 | .4818 | .5023 | .4950 | .5219 | .5237 | .5127 | .5196 |
| 5 | Reg | 3, 6, 7, 16, 21 | 3, 7, 10, 16, 21 | 3, 6, 7, 10, 14 | 3, 7, 10, 16, 21 | 1, 3, 7, 10, 16 | 1, 3, 7, 10, 16 | 1, 6, 7, 10, 14 | 1, 2, 9, 10, 16 |
| | Sen | .8764 | .8625 | .8979 | .8625 | .8888 | .8888 | .9024 | .8443 |
| | Spe | .8851 | .8935 | .8635 | .8935 | .8874 | .8874 | .8650 | .9009 |
| | Error | .1165 | .1148 | .1245 | .1148 | .1109 | .1109 | .1216 | .1156 |
| | Rej | .5087 | .4996 | .4919 | .4996 | .5145 | .5145 | .5133 | .5296 |
| 7 | Reg | 3, 5, 6, 7, 10, 16, 21 | 3, 6, 7, 10, 11, 16, 21 | 1, 5, 6, 7, 8, 10, 14 | 2, 3, 7, 10, 16, 20, 21 | 1, 3, 5, 7, 10, 11, 16 | 1, 3, 5, 7, 10, 11, 16 | 3, 5, 6, 7, 10, 11, 14 | 1, 2, 3, 9, 10, 16, 21 |
| | Sen | .8873 | .8780 | .8926 | .8556 | .8942 | .8942 | .8995 | .8415 |
| | Spe | .8847 | .8919 | .8574 | .8936 | .8896 | .8896 | .8639 | .9032 |
| | Error | .1136 | .1110 | .1310 | .1171 | .1075 | .1075 | .1237 | .1146 |
| | Rej | .5034 | .5048 | .4970 | .5041 | .5117 | .5117 | .5067 | .5228 |
| 9 | Reg | 2, 3, 5, 6, 7, 10, 16, 20, 21 | 2, 3, 5, 6, 7, 10, 16, 20, 21 | 3, 4, 5, 6, 7, 10, 11, 16, 19 | 1, 2, 3, 6, 7, 10, 16, 20, 21 | 1, 3, 5, 6, 7, 10, 11, 12, 16 | 1, 3, 5, 6, 7, 10, 11, 16, 21 | 3, 5, 6, 7, 8, 10, 11, 14, 19 | 1, 2, 6, 9, 10, 11, 16, 21, 22 |
| | Sen | .8679 | .8679 | .8819 | .8556 | .8903 | .8870 | .8904 | .8439 |
| | Spe | .8887 | .8887 | .8616 | .8918 | .8884 | .8903 | .8692 | .9034 |
| | Error | .1386 | .1386 | .1308 | .1181 | .1094 | .1088 | .1223 | .1141 |
| | Rej | .5085 | .5085 | .4968 | .5005 | .5136 | .5073 | .5005 | .5147 |

TABLE 11

Summary of results with Naive Bayes combination rule and base classifiers with .50 rejection rate.

| | | Linear Kernel | | | | RBF Kernel | | | |
|---|---|---|---|---|---|---|---|---|---|
| L | | ARR | Error | Sen | Spe | ARR | Error | Sen | Spe |
| 3 | Reg | 1, 7, 10 | 6, 10, 21 | 1, 7, 10 | 6, 11, 21 | 2, 7, 10 | 1, 10, 16 | 2, 7, 10 | 1, 10, 16 |
| | Sen | .8657 | .8657 | .8953 | .8172 | .8973 | .8585 | .9016 | .8585 |
| | Spe | .8902 | .8902 | .8488 | .9027 | .8817 | .9064 | .8479 | .9064 |
| | Error | .1160 | .1160 | .1372 | .1242 | .1122 | .1073 | .1351 | .1073 |
| | Rej | .5273 | .5273 | .5023 | .5227 | .5219 | .5237 | .5127 | .5237 |
| 5 | Reg | 3, 6, 7, 11, 16 | 3, 6, 7, 11, 16 | 3, 6, 7, 10, 14 | 3, 7, 17, 18, 21 | 1, 3, 7, 10, 16 | 1, 6, 10, 16, 18 | 1, 6, 7, 10, 14 | 1, 6, 10, 16, 18 |
| | Sen | .8855 | .8855 | .8995 | .7789 | .8888 | .8603 | .9034 | .8603 |
| | Spe | .8869 | .8869 | .8688 | .8972 | .8894 | .9036 | .8662 | .9036 |
| | Error | .1126 | .1126 | .1205 | .1407 | .1094 | .1082 | .1207 | .1082 |
| | Rej | .5060 | .5060 | .4919 | .5073 | .5145 | .5158 | .5133 | .5158 |
| 7 | Reg | 3, 6, 7, 10, 11, 16, 21 | 3, 6, 7, 10, 11, 16, 21 | 1, 5, 6, 7, 8, 10, 14 | 2, 3, 6, 10, 16, 20, 21 | 1, 3, 5, 7, 10, 11, 16 | 1, 3, 5, 7, 10, 11, 16 | 3, 5, 6, 7, 10, 11, 14 | 1, 2, 6, 11, 13, 16, 18 |
| | Sen | .8733 | .8733 | .8909 | .8440 | .8942 | .8942 | .8984 | .8348 |
| | Spe | .8948 | .8948 | .8646 | .8963 | .8935 | .8935 | .8661 | .9031 |
| | Error | .1109 | .1109 | .1267 | .1190 | .1047 | .1047 | .1227 | .1163 |
| | Rej | .5048 | .5048 | .4970 | .4950 | .5117 | .5117 | .5067 | .5120 |
| 9 | Reg | 2, 3, 5, 6, 7, 10, 16, 20, 21 | 3, 5, 6, 7, 10, 11, 16, 18, 21 | 2, 3, 5, 6, 7, 8, 10, 11, 14 | 2, 3, 6, 7, 13, 16, 18, 21, 22 | 1, 3, 5, 6, 7, 10, 11, 12, 16 | 1, 5, 6, 7, 10, 11, 16, 18, 21 | 3, 5, 6, 7, 8, 10, 11, 14, 19 | 1, 2, 6, 9, 10, 11, 16, 21, 22 |
| | Sen | .8675 | .8639 | .8788 | .8333 | .8903 | .8802 | .8915 | .8439 |
| | Spe | .8902 | .8919 | .8708 | .8943 | .8904 | .8959 | .8695 | .9052 |
| | Error | .1160 | .1158 | .1251 | .1249 | .1081 | .1074 | .1220 | .1130 |
| | Rej | .5085 | .5048 | .5101 | .5007 | .5136 | .5090 | .5005 | .5147 |

Using more base classifiers reduced the rejection rate without significantly reducing the sensitivity and specificity. This is particularly true for the cases where base classifiers with about 0.33 rejection rate were used, although it is also observable, in a lesser fashion, for cases where 0.50 were used.

The improvement gained when using the integrated approach can really be appreciated when compared against the classification results obtained using the standard approach. With the standard approach a sensitivity and specificity of 0.74 and 0.75 are obtained while using the integrated approach yields a sensitivity, specificity and rejection rate of 0.85, 0.85, 0.27 with base classifiers that have a rejection rate of around 0.33 and of 0.89, 0.89, 0.51 with base classifiers that have a rejection rate of around 0.50.

CONCLUSION

Feature extraction and feature selection methods, specifically PCA, SFFS and SVDSS, were evaluated in order to deal with the high dimensional nature of the ESS data. While no significant improvement in classification performance was observed when the different dimensionality reduction methods were applied to the test data, the use of feature selection allowed for better understanding of what areas of the ESS spectrum were more useful for classification purposes. It was seen that the shorter wavelengths were better suited for this. This observation was later confirmed as classifiers were designed on different regions of the spectrum, those designed on regions in the shorter wavelengths had comparable, and in some cases better, performance when compared to the use of the whole spectrum, as opposed to using the longer wavelengths where the classification performance was not as good.

A major challenge that arises in this application is the inherent biological variability present. This makes distinguishing pathologies, with high accuracy, particularly difficult. Using the standard paradigm of dimensionality reduction and classification on the ESS spectrum, with SVM with linear kernel, resulted in sensitivities and specificity of ~0.75. Moreover, using non-linear kernels didn't improve this result significantly, illustrating that indeed the dataset was neither linearly nor non-linearly separable. To overcome these elements the use of an error-rejection framework was used. The classifier identifies the region where samples are more likely to be misclassified and withholds from classifying, or reject, samples lying in this region. These samples can then be examined by other methods. This particular framework was adopted since it is well suited for the application of colon cancer screening. If the classifier does not make a decision on a sample, either further optical measurements can be taken or a biopsy can be taken and examined by a pathologist. In particular, the classifier is a support vector machine with embedded error-rejection was developed. Both the orientation and the width of the decision region, according to weights that reflect the tradeoff between rejecting and misclassifying samples, are obtained during the training phase. The training problem is formulated as a convex optimization problem a dual training algorithm, based on sequential minimal optimization (SMO), as well as allowing the use of kernels to obtain non-linear decision regions. Results showed that this approach yielded better results than methods that reject samples by thresholding the outputs of standard classifiers. Further improvements in the results were obtained by using non-linear kernels. When compared to the standard classification paradigm, that yielded sensitivities of ~0.74 and specificities of ~0.77 with a RBF kernel, using error-rejection a sensitivity of ~0.80 and specificity of ~0.85 with a ~0.33 rejection rate, and a sensitivity of ~0.82 and specificity of ~0.89 with a ~0.50 rejection rate can be obtained also using a RBF kernel.

Another classification methodology that was employed to improve on the performance was a multiple classifier system. The multiple classifier system makes a final decision by combining the decision of several base classifiers. Each base classifier is designed using features extracted from a different region of the ESS spectrum. The regions used were chosen heuristically, using observations and intuition gathered from the results of the feature selection experiments. It is worth noting that regions like 330-600 nm, with sensitivity and specificity of ~0.76, 330-400 nm, with sensitivity of ~0.8 and specificity of ~0.73, and 360-600 nm, with sensitivity of ~0.77 and specificity of ~0.74, showed a performance comparable, if not better, to using the whole spectrum, 330-760 nm, whose sensitivity was of ~0.74 and specificity of ~0.77. When using the ensemble classifier sensitivities and specificities of ~0.80 and ~0.78, ~0.81 and ~0.76, ~0.75 and ~0.83, and finally ~0.78 and ~0.80 could be obtained using different combinations of regions. These results clearly show an overall improvement on the performance of any given single classifier used as base classifiers.

Finally, error-rejection and multiple classifier systems were incorporated into one unified framework. This was accomplished by integrating the developed SVM with embedded error-rejection with the multiple classifiers system described above. Classifiers with error-rejection were trained on the ESS spectral regions used earlier and then combined to obtain the final decision. Again, improvement is sought over the 0.80 sensitivity, 0.85 specificity with 0.32 rejection rate, and the 0.82 sensitivity, 0.89 specificity with 0.51 rejection rate obtained using error-rejection with the whole spectrum, 330-760 nm, or other well performing regions like 330-400 nm with sensitivities, specificities and rejection rates of 0.86, 0.80, 0.32 and 0.88, 0.83, 0.49, and 360-600 nm with sensitivities, specificities and rejection rates of 0.83, 0.83, 0.33 and 0.88, 0.87, 0.53. Using the unified framework, different classifier ensembles with sensitivities, specificities and rejection rates of 0.85, 0.85, 0.27 or 0.86, 0.86, 0.33 or 0.87, 0.84, 0.29 or 0.88, 0.81, 0.32 can be obtained by base classifiers trained to have around 0.33 rejection rate. By using around 0.50 as the base classifier rejection rate, ensembles with sensitivities, specificities and rejection rates of 0.89, 0.89, 0.51 or 0.90, 0.87, 0.49 or 0.86, 0.91, 0.52 or 0.88, 0.90, 0.51 or 0.87, 0.88, 0.46 can be obtained, clearly showing improvement over single classifiers that use the whole spectrum or any individual region.

AdaBoost

The AdaBoost algorithm is a method that attempts to "boost" the accuracy of any given learning algorithm. Let $x_i \in \mathfrak{R}^d$, be an input vector and $y_i \in \{1, -1\}$ its corresponding label for $i=1, \ldots, l$, where l is the total number of training samples. The goal is to construct a decision function composed of an ensemble of classifiers, $g_t: x \mapsto \{\pm 1\}$ called base learners or weak learners, of the form:

$$f_T(x) = \sum_{t=1}^{T} c_t g_t(x). \tag{63}$$

The algorithm calls the base learner repeatedly over a series of rounds $t=1, \ldots, T$, while maintaining a distribution or set of weights over the training set. The weights of incorrectly classified samples are increased so that the weak learner focuses on the hard to classify samples. At each round t, the base learner $g_t(x)$ is applied to the training set with the current weight distribution. Then the algorithm assigns a weight to that hypothesis that intuitively measures the importance assigned to $g_t(x)$. The details of the AdaBoost training algorithm are shown in FIG. 14.

The problem of the inclusion of an error-rejection option in multiple classifier systems is a linear combination of the outputs of trained classifiers. The best error-reject trade-off achievable by a linear combination of classifiers is always not worse that that of the best single classifier. This trade-off is dependent not only in the reject threshold but also on the coefficients of the linear combination of classifiers. Thus, the problem of training a multiple classifier system with reject option is one of finding the coefficients and reject threshold given the error and rejection costs.

Embodiments of the present invention also apply error rejection to the AdaBoost classifier. Advantage was taken of the similarity between the support vector machine training problem and a formulation posed for introducing soft margins in AdaBoost. This new training problem not only seeks to obtain the rejection threshold but also to recompute the ensemble weights, thus forming the decision regions. Again, these two depend on the rejection and error costs.

AdaBoost asymptotically achieves a hard margin, i.e. the algorithm concentrates on the hard to learn pattern without allowing for errors. Thus, some sort of regularization is desirable which would enable the algorithm to mistrust data and achieve a soft margin, i.e. some errors are allowed. Empirically it was observed that the more different the hypotheses' weights, $b_t$, are the higher the complexity of the ensemble. Thus, the norm of the weight vector $\|b\|$ can be viewed as a complexity measure. If $\|b\|$ has a high value, then some of the hypotheses are strongly emphasized. In order to achieve a soft margin it would be desirable to for $\|b\|$ to have a smaller value, as this would mean that the emphasis on the hypotheses is more distributed. With this in mind and by the introduction of the slack variables $\xi_i$, the following optimization problem that finds the values of $b_t$ in order to achieve sort margins is provided:

minimize $$\|b\|^2 + C \sum_i \xi_i, \qquad (64)$$

with the following constraints $$\sum_{t=1}^{T} b_t y_i g_t(x_i) \geq 1 - \xi_i, \quad i = 1, \ldots, l, \qquad (65)$$

$$\xi_i \geq 0, \quad i = 1, \ldots, l,$$

$$b_t \geq 0, \quad t = 1, \ldots, T.$$

This problem is solved after the AdaBoost algorithm shown in FIG. 3 is run to obtain T hypothesis $g_i, \ldots, g_T$.

The training problem incorporates an error-reject option that can be formulated using functional $h_c(\xi_i, \epsilon)$, described above. The problem is to then minimize $$\|b\|^2 + C \sum_i h_c(\xi_i, \epsilon), \qquad (66)$$

with constraints $$\sum_{t=1}^{T} b_t y_i g_t(x_i) \geq 1 - \xi_i, \quad i = 1, \ldots, l, \qquad (67)$$

-continued $$\xi_i \geq 0, \quad i = 1, \ldots, l,$$

$$b_t \geq 0, \quad t = 1, \ldots, T,$$

$$0 \leq \epsilon \leq 1.$$

The decision function is then obtained as follows:

$$f(x) = \begin{cases} +1, & \text{if } \sum_{t=1}^{T} b_t g_t(x) \geq \epsilon \\ -1, & \text{if } \sum_{t=1}^{T} b_t g_t(x) \leq -\epsilon \\ 0, & \text{if } -\epsilon < \sum_{t=1}^{T} b_t g_t(x) < \epsilon. \end{cases} \qquad (68)$$

Thus, in order to achieve error-rejection in an ensemble classifier, the ensemble weights and reject threshold are computed given the costs of rejecting and misclassifying samples.

Unless specifically stated otherwise, throughout the present disclosure, terms such as "processing", "computing", "calculating", "determining", or the like, may refer to the actions and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include an apparatus for performing the operations therein. Such apparatus may be specially constructed for the desired purposes, or it may comprise a general-purpose computer selectively activated or reconfigured by a computer program stored in the computer.

Figure 15:
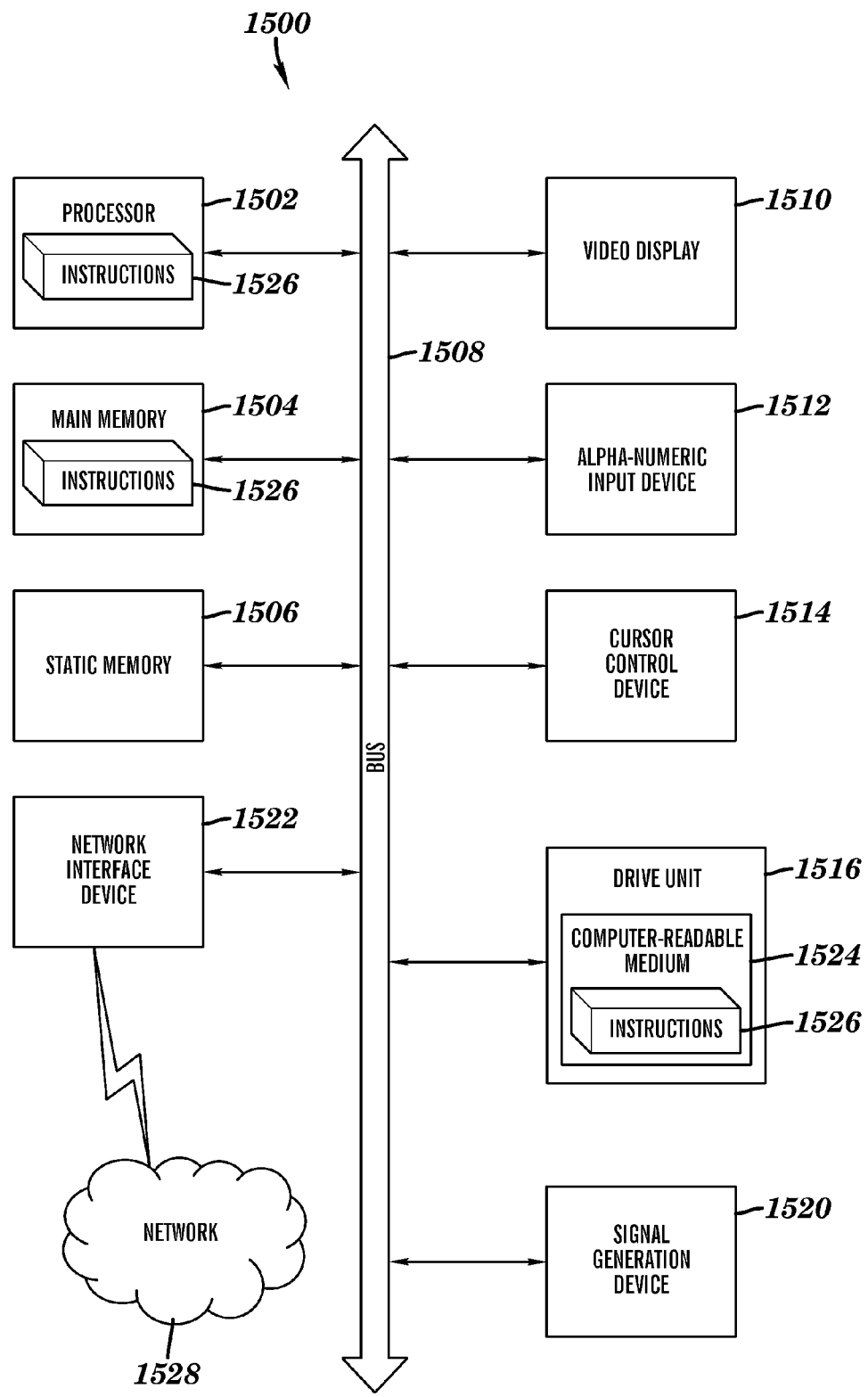
FIG. 15 is a block diagram of an exemplary computer system.

FIG. 15 shows a diagrammatic representation of a machine in the exemplary form of a computer system 1500 within which a set of instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server, personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 1500 includes a processor 1502 (e.g., a central processing unit (CPU), a graphics processing unit (GPU) or both), a main memory 1504 (e.g., read only memory (ROM), flash memory, dynamic random access memory (DRAM) such as synchronous DRAM (SDRAM) or Rambus DRAM (RDRAM), etc.) and a static memory 1506

(e.g., flash memory, static random access memory (SRAM), etc.), which communicate with each other via a bus 1508.

The computer system 1500 may further include a video display unit 1510 (e.g., a liquid crystal display (LCD) or a cathode ray tube (CRT)). The computer system 1500 also includes an alphanumeric input device 1512 (e.g., a keyboard), a cursor control device 1514 (e.g., a mouse), a disk drive unit 1516, a signal generation device 1520 (e.g., a speaker) and a network interface device 1522.

The disk drive unit 1516 includes a machine-readable medium 1524 on which is stored one or more sets of instructions (e.g., software 1526) embodying any one or more of the methodologies or functions described herein. The software 1526 may also reside, completely or at least partially, within the main memory 1504 and/or within the processor 1502 during execution of the software 1526 by the computer system 1500.

The software 1526 may further be transmitted or received over a network 1528 via the network interface device 1522.

While the machine-readable medium 1524 is shown in an exemplary embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier waves. The term "machine-readable storage medium" shall accordingly be taken to include, but not be limited to, solid-state memories and optical and magnetic media (e.g., any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions or data, and capable of being coupled to a computer system bus).

The invention has been described through functional modules, which are defined by executable instructions recorded on computer readable media which cause a computer to perform method steps when executed. The modules have been segregated by function for the sake of clarity. However, it should be understood that the modules need not correspond to discreet blocks of code and the described functions can be carried out by the execution of various code portions stored on various media and executed at various times.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the present invention.

Moreover, other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A system configured to classify a tissue pathology comprising:

an optical probe configured to measure the biomedical optical spectra data from a tissue; and a classification system coupled to the optical probe comprising a plurality of support vector machines with embedded error rejection to classify the biomedical optical spectra data from the tissue; wherein each of the plurality of the support vector machines with embedded error rejection is configured to classify a different region of the optical spectra data from the tissue, the classification comprising:

using feature selection to determine the regions of greatest difference between the average spectrum for dysplastic and non-dysplastic tissues classifying a first region of the biomedical optical spectra data from the tissue using a first classifier;

classifying a second region of the biomedical optical spectra data from the tissue using a second classifier, the first region being different than the second region; and combining the classification of the first classifier with the classification of the second classifier to determine a classification of the tissue, wherein the first and the second classifier cover optical spectra data from wavelength 330-600 nm and/or 330-400 nm;

wherein the classification of the first classifier and the classification of the second classifier is selected from the group consisting of positive, negative and rejected.

2. The system of claim 1 wherein the optical probe is an integrated biopsy forceps tool.

3. The system of claim 2 wherein the integrated biopsy forceps tool comprises an illuminating optical fiber to direct light at tissue to be imaged and a collecting optical fiber to collect the light scattered in the tissue.

4. The system of claim 1 wherein the biomedical optical spectra data is elastic-scattering spectroscopy (ESS) data.

5. The system of claim 1 wherein the first classifier and the second classifier are configured to classify the first and second regions using a decision function wherein the decision function comprises:

$$f(x) = \begin{cases} +1, & \text{if } w^T x - b \geq \varepsilon \\ -1, & \text{if } w^T x - b \leq -\varepsilon \\ 0, & \text{if } -\varepsilon < w^T x - b < \varepsilon. \end{cases}$$

6. The system of claim 1 wherein the first classifier and the second classifier are configured to classify the first and second regions using a decision function wherein the decision function comprises:

$$f(x) = \begin{cases} +1, & \text{if } \sum_i \alpha_i y_i K(x_i, x) - b \geq \varepsilon \\ -1, & \text{if } \sum_i \alpha_i y_i K(x_i, x) - b \leq -\varepsilon \\ 0, & \text{if } -\varepsilon < \sum_i \alpha_i y_i K(x_i, x) - b < \varepsilon. \end{cases}$$

7. A method for classifying a tissue comprising:
receiving by a classification system biomedical optical spectra data for the tissue;
using feature selection to determine regions of greatest difference between the average spectrum for dysplastic and non-dysplastic tissues
classifying, using the classification system, a first region of the biomedical optical spectra data from wavelengths between 330 and 600 nm and/or between 330 and 400 nm using a first classifier;
classifying, using the classification system, a second region of the biomedical optical spectra data from wavelengths between 330-600 nm and/or between 330-400 nm using a second classifier, the first region being different than the second region; and
combining the classification of the first classifier with the classification of the second classifier to determine a classification of the tissue;
wherein the classification of the first classifier and the classification of the second classifier is selected from the group consisting of positive, negative and rejected.

8. The method of claim 7, further comprising performing an optical spectroscopy on a tissue to obtain biomedical optical spectra data for the tissue.

9. The method of claim 7, wherein the biomedical optical spectra data comprises elastic-scattering spectroscopy (ESS) data.

10. The method of claim 7, wherein the first region overlaps the second region.

11. The method of claim 7, further comprising classifying a third region of the biomedical optical spectra data using a third classifier and wherein the classification of the third classifier is combined with the classification of the first classifier and the classification of the second classifier to determine the classification of the tissue.

12. The method of claim 7, wherein said classifying the first region comprises withholding from classifying the first region.

13. The method of claim 7, wherein said classifying the second region comprises withholding from classifying the second region.

14. The method of claim 7, wherein the first classifier and the second classifier are support vector machines.

15. The method of claim 7, wherein the first classifier and the second classifier are support vector machines embedded with error rejection.

16. The method of claim 7, wherein said combining the classification of the first classifier with the classification of the second classifier comprises using a majority voting rule, or using a naïve Bayes rule.

17. The method of claim 7, wherein the first classifier and the second classifier are configured to classify the first and second regions using a decision function, wherein the decision function comprises:

$$f(x) = \begin{cases} +1, & \text{if } w^T x - b \geq \varepsilon \\ -1, & \text{if } w^T x - b \leq -\varepsilon \\ 0, & \text{if } -\varepsilon < w^T x - b < \varepsilon. \end{cases}$$

18. The method of claim 7, wherein the first classifier and the second classifier are configured to classify the first and second regions using a decision function, wherein the decision function comprises:

$$f(x) = \begin{cases} +1, & \text{if } \sum_i \alpha_i y_i K(x_i, x) - b \geq \varepsilon \\ -1, & \text{if } \sum_i \alpha_i y_i K(x_i, x) - b \leq -\varepsilon \\ 0, & \text{if } -\varepsilon < \sum_i \alpha_i y_i K(x_i, x) - b < \varepsilon. \end{cases}$$

19. A machine readable storage medium comprising instructions executable by a data processing machine to perform a method for classifying a tissue, the method comprising:
using feature selection to determine regions of greatest difference between the average spectrum for dysplastic and non-dysplastic tissues
classifying a first region of biomedical optical spectra data from wavelengths between 330-600 nm and/or between 330-400 nm using a first classifier;
classifying a second region of biomedical optical spectra data from wavelengths between 330-600 nm and/or between 330-400 nm using a second classifier, the first region being different than the second region; and
combining the classification of the first classifier with the classification of the second classifier to determine a classification of the tissue;
wherein the classification of the first classifier and the classification of the second classifier is selected from the group consisting of positive, negative and rejected.

20. A system for classifying a tissue comprising: memory and a processor configured to execute instructions for:
using feature selection to determine regions of greatest difference between the average spectrum for dysplastic and non-dysplastic tissues
classifying a first region of biomedical optical spectra data from wavelengths between 330-600 nm and/or between 330-400 nm;
classifying a second region of biomedical optical spectra data from wavelengths between 330-600 nm and/or between 330-400 nm, the first region being different than the second region; and
combining the classification of the first region with the classification of the second region to determine a classification of the tissue sample,
wherein the classification of the first region and the classification of the second region is selected from the group consisting of positive, negative and rejected.

* * * * *